(12) United States Patent
Suganuma et al.

(10) Patent No.: US 7,683,195 B2
(45) Date of Patent: Mar. 23, 2010

(54) SILVER β-KETOCARBOXYLATE, MATERIAL COMPRISING THE SAME FOR FORMING SILVER METAL, AND USE THEREOF

(75) Inventors: Katsuaki Suganuma, Osaka (JP); Shunro Yamaguchi, Osaka (JP); Mariko Hatamura, Osaka (JP)

(73) Assignees: Osaka Industrial Promotional Organization, Osaka (JP); Osaka University, Osaka (JP)

( * ) Notice: Subject to any disclaimer, the term of this patent is extended or adjusted under 35 U.S.C. 154(b) by 177 days.

(21) Appl. No.: 11/988,247

(22) PCT Filed: Jun. 22, 2006

(86) PCT No.: PCT/JP2006/312539
§ 371 (c)(1),
(2), (4) Date: Jan. 3, 2008

(87) PCT Pub. No.: WO2007/004437
PCT Pub. Date: Jan. 11, 2007

(65) Prior Publication Data
US 2009/0209693 A1 Aug. 20, 2009

(30) Foreign Application Priority Data
Jul. 4, 2005 (JP) .............................. 2005-195320

(51) Int. Cl.
*C07C 49/92* (2006.01)
*C07F 1/10* (2006.01)
*C23C 16/00* (2006.01)

(52) U.S. Cl. ..................... 556/40; 427/255.28; 556/114

(58) Field of Classification Search .................... 556/40, 556/114; 427/255.28
See application file for complete search history.

(56) References Cited

U.S. PATENT DOCUMENTS

| 2,678,953 | A | 5/1954 | Conly |
| 6,358,611 | B1 | 3/2002 | Nagasawa et al. |
| 7,507,517 | B2 * | 3/2009 | Wolfe et al. ............ 430/137.14 |
| 2003/0087185 | A1 * | 5/2003 | Chung et al. ............. 430/270.1 |

FOREIGN PATENT DOCUMENTS

| JP | 51-122011 | 10/1976 |
| JP | 10-183207 | 7/1998 |
| JP | 11-172454 | 6/1999 |
| JP | 2003-191646 | 7/2003 |
| JP | 2004-214236 | 7/2004 |
| JP | 2004-315374 | 11/2004 |
| WO | 01/11955 | 2/2001 |

* cited by examiner

*Primary Examiner*—Porfirio Nazario Gonzalez
(74) *Attorney, Agent, or Firm*—Hamre, Schumann, Mueller & Larson, P.C.

(57) ABSTRACT

It is an object to provide a novel material that can quickly form metal silver even at a low temperature of approximately 210° C. or less. This serves as a metal silver forming material that includes a silver β-ketocarboxylate. By heating this forming material, it is possible to form metal silver quickly even at a low temperature of approximately 210° C. or less. Examples of the silver β-ketocarboxylate include silver isobutyrylacetate, silver benzoylacetate, silver acetoacetate, silver propionylacetate, silver α-methylacetoacetate, and silver α-ethylacetoacetate.

23 Claims, 9 Drawing Sheets

SILVER β-KETOCARBOXYLATE, MATERIAL COMPRISING THE SAME FOR FORMING SILVER METAL, AND USE THEREOF

TECHNICAL FIELD

The present invention relates to silver β-ketocarboxylates, materials comprising the same for forming silver metal, methods of producing silver metals using the same, and silver metals using the same.

BACKGROUND ART

Silver metal is widely used as a recording material and printing plate material, and it also is used as a high conductivity material due to its excellent conductivity. A general method for producing silver metal is to heat silver oxide, which is an inorganic substance, in the presence of a reducing agent. Specifically, silver oxide powder is dispersed in a binder and a reducing agent is added thereto to prepare a paste, and the paste is then applied to a base material or the like and heated. In this way, the silver oxide is reduced by heating in the presence of a reducing agent, and the silver metal that is produced by this reduction fuses to form a film that includes silver metal.

However, the problem with the use of silver oxide as a material for forming silver metal is that it requires a reducing agent as well as a very high processing temperature of approximately 300° C. Moreover, if the silver metal is to be used as conducting material, then it is necessary to use finer silver oxide particles in order to lower the resistance of the film that is formed.

On the other hand, recently there have been reported methods of forming silver metal using organic acid silver instead of inorganic compounds as mentioned above. An example of an organic acid silver that has been reported is silver behenate (Patent Document 1), and silver stearate and silver α-ketocarboxylate also have been reported as new materials for forming silver metals (Patent Documents 2 and 3).

Patent Document 1: JP 2003-191646 A
Patent Document 2: JP H10-183207 A
Patent Document 3: JP 2004-315374 A

DISCLOSURE OF INVENTION

Problem to be Solved by the Invention

However, when silver behenate is used, it is necessary to conduct the heating in the presence of a reducing agent in order to generate the silver metal. Likewise, although heating temperature is lower than with inorganic compounds, when silver stearate or silver α-ketocarboxylate are used, it is necessary to conduct heating at approximately 210° C. or more in order to rapidly effect decomposition.

Accordingly, it is an object of the invention to provide a novel material that can rapidly form metal silver even at a low temperature of approximately 210° C. or less.

Means for Solving Problem

To achieve this object, a novel compound of the invention is a silver β-ketocarboxylate represented by Formula (1) below:

[Chemical Formula 1]

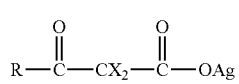

(1)

In Formula (1), R is a straight, branched or cyclic saturated or unsaturated $C_1$ to $C_{20}$ aliphatic hydrocarbon group, $R^1$—$CY_2$—, $CY_3$—, $R^1$—$CHY$—, $R^2O$—, a phenyl group, a phenyl group with one or more substituent groups, $R^5R^4N$—, a hydroxyl group (—OH), an amino group (—$NH_2$), or ($R^3$O)$_2$CY—. However, the Y groups are identical or different, and each is a fluorine atom, a chlorine atom, a bromine atom, or a hydrogen atom, $R^1$ is a straight, branched or cyclic saturated or unsaturated $C_1$ to $C_{19}$ aliphatic hydrocarbon group, or a phenyl group, $R^2$ is a straight, branched or cyclic saturated or unsaturated $C_1$ to $C_{20}$ aliphatic hydrocarbon group, $R^3$ is a straight, branched or cyclic saturated or unsaturated $C_1$ to $C_{16}$ aliphatic hydrocarbon group, and $R^4$ and $R^5$ are identical or different, and each is a straight, branched or cyclic saturated or unsaturated $C_1$ to $C_{18}$ aliphatic hydrocarbon group.

In Formula (1), the X groups are identical or different, and each is a hydrogen atom, a straight, branched or cyclic saturated or unsaturated $C_1$ to $C_{20}$ aliphatic hydrocarbon group, $R^6O$—, $R^6S$—, $R^6$—CO—, $R^6$—CO—O—, a halogen (fluorine, chlorine, bromine, iodine), a benzyl group, a phenyl group, a phenyl group or a benzyl group that has one or more substituent groups, a cyano group (—C≡N), a N-phthaloyl-3-aminopropyl group, or a 2-ethoxyvinyl group ($C_2H_5$—O—CH═CH—).

And, $R^6$ is a straight, branched or cyclic saturated or unsaturated $C_1$ to $C_{10}$ aliphatic hydrocarbon group, a thiophene group ($C_4H_3S$—), a phenyl group, a diphenyl group, or a phenyl group or a diphenyl group that has one or more substituent groups.

A metal silver forming material of the invention is characterized in that it includes silver β-ketocarboxylate. A method of producing metal silver of the invention is characterized in that it includes a step of heating a material for forming metal silver, in which the forming material is the forming material that includes the silver β-ketocarboxylate of the invention.

A method of producing silver β-ketocarboxylate of the invention is a method of producing silver β-ketocarboxylate including a step of reacting a β-ketocarboxylic acid and a silver compound in a reaction solution whose water content is not more than 55 wt % in order to form a silver β-ketocarboxylate.

EFFECTS OF THE INVENTION

The metal silver forming material of the invention, for example, allows for the rapid decomposition to metal silver at a low temperature of approximately 210° C. or less without the presence of a catalyst. In this way it is different from conventional metal silver forming materials in that it does not require a catalyst or processing at high temperatures in excess of 210° C. in order to effect decomposition to the metal silver, the metal silver production method of the invention, which uses the forming material of the invention, readily can form metal silver at a low temperature of approximately 210° C. or less without the presence of a catalyst. Moreover, because it is possible to form metal silver at a low temperature, it also becomes possible to form metal silver on a resin base material with a low heat resistance, and because the silver β-ketocarboxylate is organic, it can be blended with resin easily, for example. Thus, the metal silver forming material and production method of the invention can be considered to further broaden the applications of metal silver. In particular, the silver β-ketocarboxylate that is represented by Formula (1) is a novel compound that was first synthesized by the present inventors, and is extremely useful as a silver β-ketocarboxylate in the metal silver forming material of the invention.

It should be noted that this mechanism of creating silver by thermal decomposition of the silver β-ketocarboxylate alone is completely different from the conventional mechanisms that require a reducing agent such as with silver behenate.

DESCRIPTION OF THE INVENTION

Figure 1:
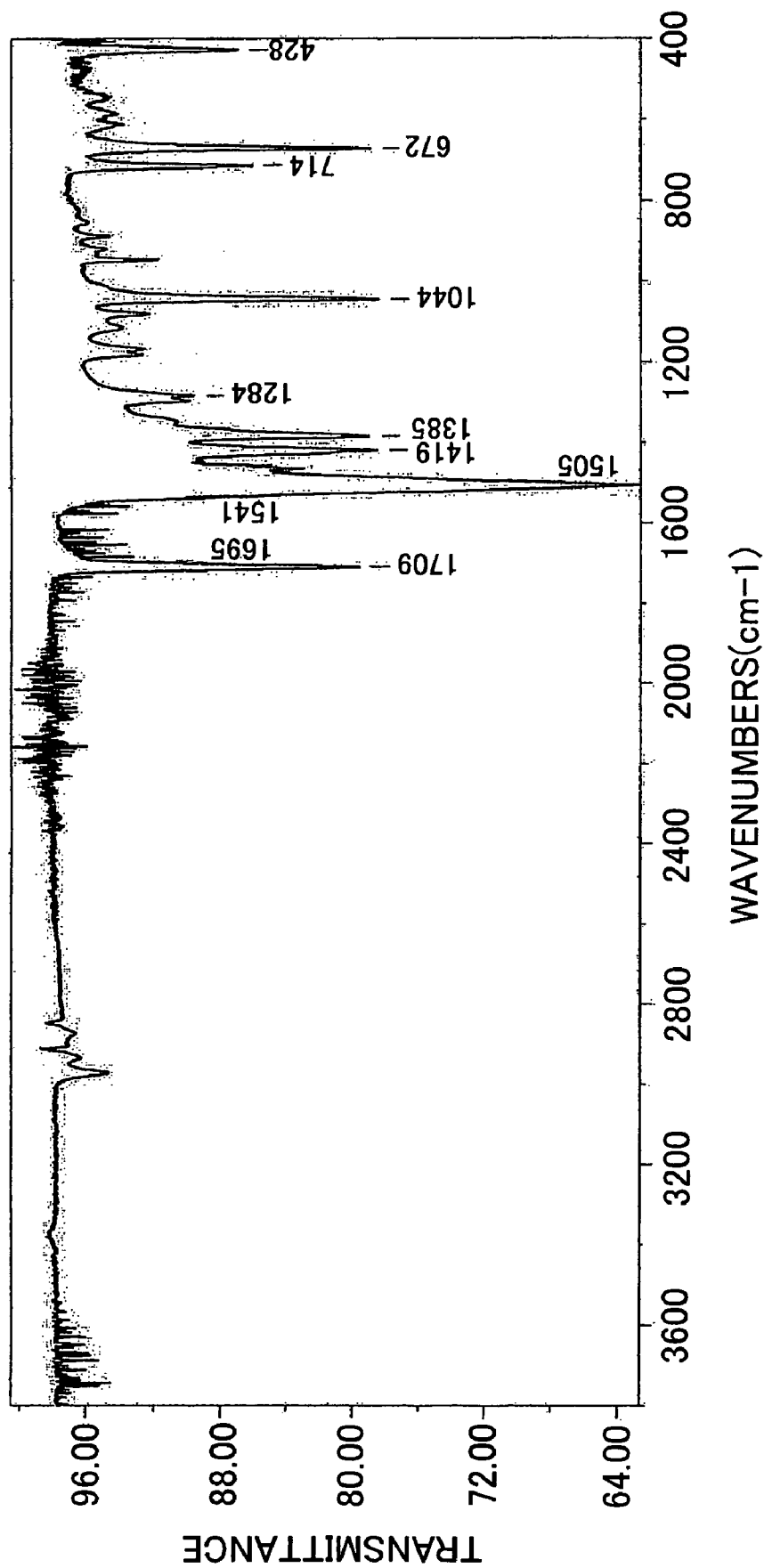
FIG. 1 is a graph showing the infrared absorption spectrum of silver isobutyrylacetate in an example of the invention.

As discussed above, the material for forming the metal silver of the invention is characterized in that it includes a silver β-ketocarboxylate. The presence of a β-ketocarbonyl group allows for rapid decomposition even at the low temperatures discussed above, and thus there are no particular limitations regarding the specific structure as long as the compound is a silver β-ketocarboxylate.

Examples of silver β-ketocarboxylates include the compounds represented by Formula (1) below. It should be noted that these compounds are novel compounds that were first synthesized by the inventors, as alluded to above.

[Chemical Formula 2]

$$R-\overset{O}{\underset{\|}{C}}-CX_2-\overset{O}{\underset{\|}{C}}-OAg \quad (1)$$

In Formula (1), R is a straight, branched or cyclic saturated or unsaturated $C_1$ to $C_{20}$ aliphatic hydrocarbon group, $R^1-CY_2-$, $CY_3-$, $R^1-CHY-$, $R^2O-$, a phenyl group, a phenyl group with one or more substituent groups, $R^5R^4N-$, a hydroxyl group (—OH), an amino group (—NH$_2$), or ($R^3O)_2CY-$.

If R is straight, branched or cyclic saturated or unsaturated $C_1$ to $C_{20}$ aliphatic hydrocarbon group, then possible examples of R include an alkyl group, an alkenyl group, an alkynyl group, a cycloalkyl group, and a cycloalkenyl group, and it may also be a group represented by $C_nH_{2n+1}$, $-C_nH_{2n-1}$, or $-C_nH_{2n-3}$ (where n is an integer from 1 to 20). It is also possible for one or more hydrogen groups of the straight, branched or cyclic saturated or unsaturated $C_1$ to $C_{20}$ aliphatic hydrocarbon group to be substituted with a fluorine atom, a chlorine atom, or a bromine atom.

If R is a substituted phenyl group, then examples of substituent groups includes $R^3-$, $R^3O-$, a fluorine atom, a chlorine atom, a bromine atom, a hydroxyl group (—OH), a cyano group (—C≡N), and a phenoxy group ($C_6H_5-O-$), and any one of the o, m, or p positions of the phenyl group may be substituted.

The Y groups in R may be identical or different, and each Y may be a fluorine atom, a chlorine atom, a bromine atom, or a hydrogen atom.

$R^1$ in R is a straight, branched or cyclic saturated or unsaturated $C_1$ to $C_{19}$ aliphatic hydrocarbon group, or a phenyl group. Examples of the hydrocarbon group include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 19).

$R^2$ is a straight, branched or cyclic saturated or unsaturated $C_1$ to $C_{20}$ aliphatic hydrocarbon group. Examples of the hydrocarbon group include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 20).

$R^3$ is a straight, branched or cyclic saturated or unsaturated $C_1$ to $C_{16}$ aliphatic hydrocarbon group. Examples of the hydrocarbon group include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 16).

$R^4$ and $R^5$ may be the same or different, and each is a straight, branched or cyclic saturated or unsaturated $C_1$ to $C_{16}$ aliphatic hydrocarbon group. Examples of the hydrocarbon group include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 18).

In Formula (1), the X groups may be the same or different, and may be a hydrogen atom or a straight, branched or cyclic saturated or unsaturated $C_1$ to $C_{20}$ aliphatic hydrocarbon group, $R^6O-$, $R^6S-$, $R^6-CO-$, $R^6-CO-O-$, a halogen (fluorine, chlorine, bromine, iodine), a benzyl group, a phenyl group, a phenyl group or a benzyl group that has one or more substituent groups, a cyano group (—C≡N), a N-phthaloyl-3-aminopropyl group, or a 2-ethoxyvinyl group ($C_2H_5-O-CH=CH-$). And, $R^6$ is a straight, branched or cyclic saturated or unsaturated $C_1$ to $C_{10}$ aliphatic hydrocarbon group, a thiophene group ($C_4H_3S-$), a phenyl group, a diphenyl group, or a phenyl group or a diphenyl group that has one or more substituent groups.

If X is a substituted phenyl group, benzyl group, or diphenyl group, then possible substituents include halogen (fluorine, chlorine, bromine, iodine) and a nitro group (—NO$_2$), and any one of the o, m, or p positions may be substituted.

If X is a straight, branched or cyclic saturated or unsaturated $C_1$ to $C_{20}$ aliphatic hydrocarbon group, then examples of X include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 20).

When X is $R^6O-$, $R^6S-$, $R^6-CO-$, or $R^6-CO-O-$, examples of $R^6$ include an alkyl group, an alkenyl group, an alkynyl group, a cycloalkyl group, and a cycloalkenyl group, and for example, it can be a group that is represented by $-C_nH_{2n+1}$, $-C_nH_{2n-1}$, or $-C_nH_{2n-3}$ (where n is an integer from 1 to 10). As mentioned above, $R^6$ may also be a thiophene group ($C_4H_3S-$), a phenyl group, a diphenyl group, or a phenyl group or a diphenyl group that has one or more substituent groups. Examples of substituents include halogens (fluorine, chlorine, bromine, iodine), and any one of the o, m, or p positions may be substituted.

In Formula (1), it is possible for one of the Xs to have a structure in which it is not joined to a group and the other X only is joined to $=CH-C_6H_4-NO_2$.

It should be noted that in this invention, there are no particular limitations regarding the "alkyl group," and examples thereof include a methyl group, an ethyl group, an n-propyl group, an isopropyl group, an n-butyl group, an isobutyl group, a sec-butyl group, and a tert-butyl group, and there are no particular limitations regarding the "alkenyl group," and examples thereof include a vinyl group, an aryl group, a 1-propenyl group, an isopropenyl group, a 1-butenyl group, and a 2-butenyl group. There are no particular limitations regarding the "alkynyl group," and examples thereof include an ethynyl group and a propargyl group, there are no particular limitations regarding the "cycloalkyl group," and examples thereof include a cyclopentyl group and a cyclohexyl group, and there are no particular limitations regarding the "cycloalkenyl group," and examples thereof include a 1,3-cyclohexadienyl group, a 1,4-cyclohexadienyl group, and a cyclopentadienyl group. In the various hydrocarbon groups of the invention, one or more hydrogen groups may be substituted with a fluorine atom, a chlorine atom, or a bromine atom.

Specific examples of the silver β-ketocarboxylate include silver isobutyrylacetate, silver benzoylacetate, silver acetoacetate, silver propionylacetate, silver α-methylacetoacetate, silver α-ethylacetoacetate, and silver α-n-butylacetoacetate. Of the compounds that are represented by Formula (1), these silver β-ketocarboxylates are particularly preferable because, as will be discussed later, when effecting decomposition to the metal silver, they allow the concentration of starting material and impurities that persist in the metal silver that is obtained to be sufficiently reduced. There is the excellent effect that the fewer impurities that the metal silver has, the better the contact is between the silver that is precipitated, the better the conductivity, and the lower the resistance.

The temperature at which the silver β-ketocarboxylate is decomposed can be set for example in the range of approximately 60° C. to 210° C., preferably in the range of approximately 60° C. to 200° C., and for example it can be adjusted according to the type of substituent groups on R or X in Formula (1).

The decomposition temperature for example depends on the ability of R to withdraw electrons, and the larger the value is the more likely a decarboxylation of the β-ketocarboxylate will occur during heating. Thus, setting R so that its electron withdrawing ability is relatively large allows the decomposition temperature to be set relatively low, for example. Conversely, setting R so that its electron withdrawing ability is relatively small allows the decomposition temperature to be set relatively high.

Below is shown an example of the relationship between the substituent group R in Formula (1) and the decomposition temperature of the silver β-ketocarboxylate. It should be noted that in Formula (1), each X is a hydrogen atom, and the equal and inequality signs in the table indicate an example of their relationship with respect to the decomposition temperature.

TABLE 1

| decomposition temperature T | R(X—H) |
|---|---|
| $60 \leq T < 80$ | $R^1-CY_2->CY_3-$ |
| $80 \leq T < 100$ | $R^1-CHY->$ chlorophenyl ≈ fluorophenyl |
| $100 \leq T < 120$ | methyl |
| $120 \leq T < 140$ | 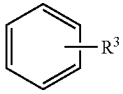 $>$ phenyl ≈ ethyl ≈ butyl |
| $140 \leq T < 160$ | isopropyl ≈ tert-butyl |
| $160 \leq T < 180$ | 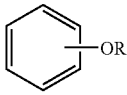 $>$ straight, branched or cyclic saturated or unsaturated $C_5$ to $C_{20}$ aliphatic hydrocarbon |
| $180 \leq T < 200$ | $R^5\!\!\diagdown\!\!N-$ $R^4\!\!\diagup$    $>$ methoxy ≈ $R^2O-$ |

Specific examples of a case where R is $R^1-CY_2-$ are shown by the groups in the formula below, and the inequality signs in the formula illustrate an example of the relationship between the decomposition temperatures of compounds that have this R.

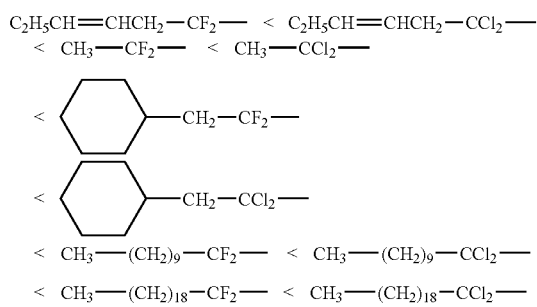

[Chemical Formula 3]

Specific examples of a case where R is $CY_3-$ include $CF_3-$ and $CCl_3-$, for example, and the relationship between the decomposition temperatures of the compounds that have this R is $CF_3$-$<CCl_3-$, for example.

Specific examples of a case where R is $R^1-CHY-$ are shown by the groups in the formula below, and the inequality signs in the formula illustrate an example of the relationship between the decomposition temperatures of compounds that have this R.

[Chemical Formula 4]

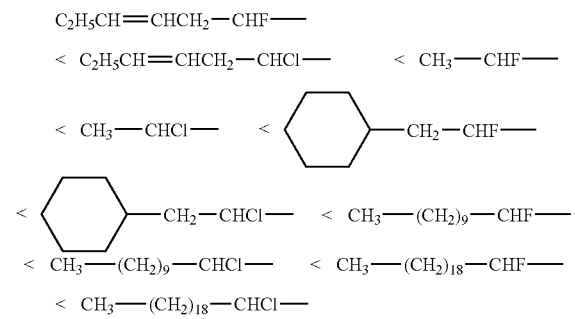

Specific examples of a case where R is a phenyl group substituted by R³— are shown by the groups in the formula below, and the inequality signs in the formula illustrate an example of the relationship between the decomposition temperatures of compounds that have this R.

[Chemical Formula 5]

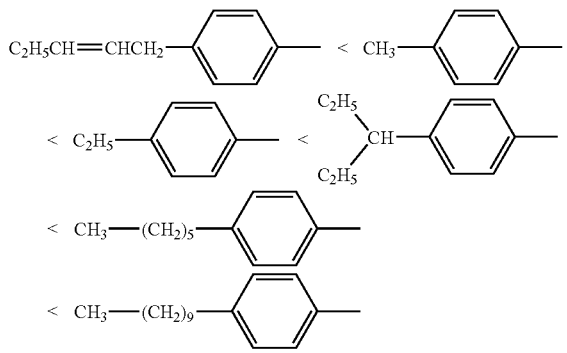

Specific examples of a case where R is a phenyl group substituted by R³O— are shown by the groups in the formula below, and the inequality signs in the formula illustrate an example of the relationship between the decomposition temperatures of compounds that have this R.

[Chemical Formula 6]

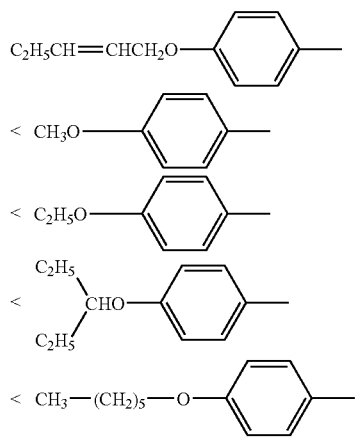

-continued

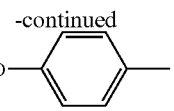

Specific examples when R is a straight, branched or cyclic saturated or unsaturated $C_1$ to $C_{20}$ aliphatic hydrocarbon group are shown by the groups in the formula below, and the inequality signs in the formula illustrate an example of the relationship between the decomposition temperatures of compounds that have this R.

[Chemical Formula 7]

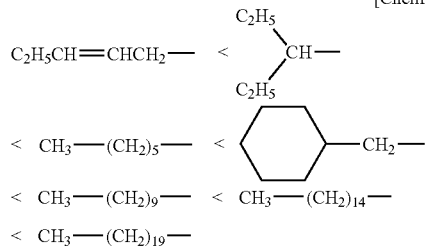

Specific examples when R is $R^5R^4N$— are shown by the groups in the formula below, and the inequality signs in the formula illustrate an example of the relationship between the decomposition temperatures of compounds that have this R.

[Chemical Formula 8]

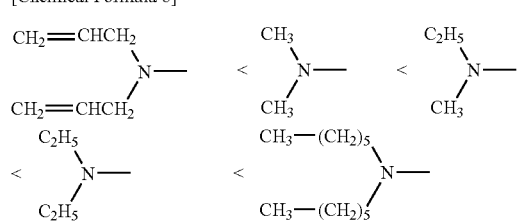

As for specific examples of the relationship between R and the decomposition temperature in a case where both Xs are hydrogen atoms, when R in Formula (1) is an isopropyl group, then the silver β-ketocarboxylate becomes silver isobutyrylacetate and has a decomposition temperature of approximately 145° C., and when R is a methyl group, then the silver β-ketocarboxylate becomes silver acetoacetate and has a decomposition temperature of approximately 110° C. Further, when R in Formula (1) is an ethyl group, then the silver β-ketocarboxylate becomes silver propionylacetate and has a decomposition temperature of approximately 130° C., and when R is a phenyl group, then the silver β-ketocarboxylate becomes silver benzoylacetate and has a decomposition temperature of approximately 120° C.

It should be noted that the extremely excellent effects described above that are obtained by using a silver β-ketocarboxylate were found first by the present inventors, among others, but the ability of the various substituent groups to withdraw electrons, and the relative relationship between the substituent groups, can be chosen with technical common sense, and thus R in Formula (1) is not limited to the examples illustrated above. In other words, for example, if R is a substituent with a smaller electron withdrawing ability than an isopropyl group, then the decomposition temperature can be set higher, whereas if R is a substituent with a greater electron withdrawing ability than an isopropyl group, then the decomposition temperature can be set lower.

The decomposition temperature of the silver β-ketocarboxylate also can be adjusted with the X in Formula (1). The larger the electron withdrawing ability of X, the more likely it is that the β-ketocarboxylic acid will undergo a decarboxylation reaction when heated. Thus, it is possible to set a relatively low decomposition temperature by choosing an X with a relatively high electron withdrawing ability. On the other hand, a relatively high decomposition temperature can be set by choosing an X with a relatively low electron withdrawing ability.

The decomposition temperature of the silver β-ketocarboxylate also can be adjusted based on the steric effects of X, such as steric hindrance. In other words, it is possible to set a relatively low decomposition temperature if an X with relatively large steric hindrance is chosen, whereas a relatively high decomposition temperature can be set if an X with relatively little steric hindrance is chosen. It should be noted that the degree of steric hindrance of the various substituent groups X, and the relative relationship of the steric hindrance among substituent groups, can be chosen from technical common sense.

The table below shows an example of the change in decomposition temperature due to substitution of X, with respect to a case in which X is a hydrogen atom in Formula (1), taking into account the electrical effect of the substituent group, such as its electron withdrawing ability, and the steric effect, such as steric hindrance. It should be noted that the degree to which the decomposition temperature changes due to the substitution of X can be regarded as being set as the value that is obtained by adding the change in temperature due to steric effects to the change in temperature due to electric effects.

TABLE 2

|  | change in decomposition temperature | | | |
| --- | --- | --- | --- | --- |
|  | mono-substitution (—CHX—) | | di-substitutions (—CX$_2$—) | |
| X | electrical effect | steric effect | electrical effect | steric effect |
| straight, branched or cyclic saturated or unsaturated C$_1$ to C$_{20}$ aliphatic hydrocarbon group | +10° C. | −20° C.~ −40° C. | +20° C. | −40° C.~ −60° C. |
| R$^6$O—, R$^6$S— | +20° C. | −30° C.~ −40° C. | +30° C. | −50° C.~ −60° C. |
| halogen, phenyl | −40° C. | −10° C.~ −30° C. | −80° C. | −30° C.~ −50° C. |
| benzyl | +5° C. | −20° C. | +10° C. | −40° C. |

Specifically, if in Formula (1) R is an isopropyl group and both Xs are hydrogen atoms, for example, then as mentioned above, the decomposition temperature of the silver isobutyrylacetate is approximately 145° C. Here, it can be understood that if only one of the Xs in Formula (1) is substituted by benzyl, then the decomposition temperature of the silver isobutyryl carboxylate can be set to approximately (145+5−20)° C., that is, 130° C., whereas if both Xs are substituted with benzyl, then the decomposition temperature can for example be set to approximately (145+10−40)° C., that is, 115° C.

Specific examples where X is R$^6$O— are shown by the groups in the formula below.

[Chemical Formula 9]

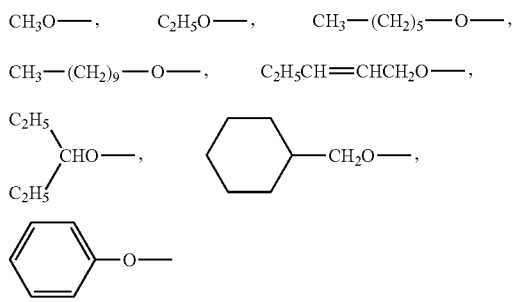

Specific examples where X is R$^6$S— are shown by the groups in the formula below.

[Chemical Formula 10]

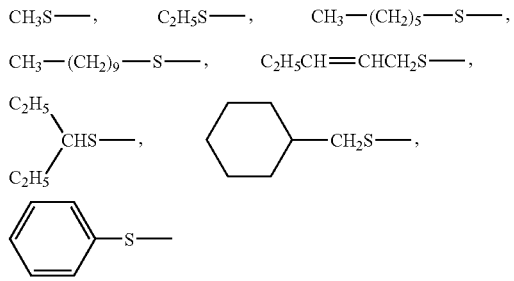

Specific examples where X is a straight, branched or cyclic saturated or unsaturated C$_1$ to C$_{20}$ aliphatic hydrocarbon group are shown by the groups in the formula below.

[Chemical Formula 11]

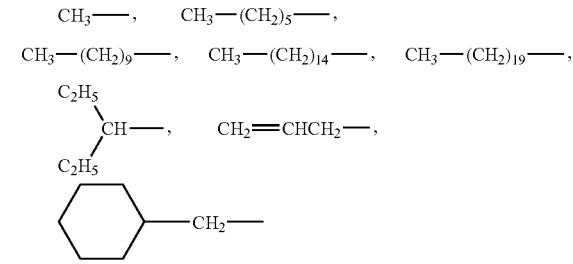

Other specific examples of R and X in Formula (1) are shown below, but there is no limitation to these.

[Chemical Formula 12]

<Specific Examples of R>

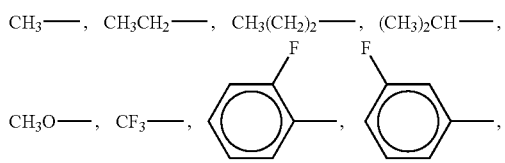

-continued

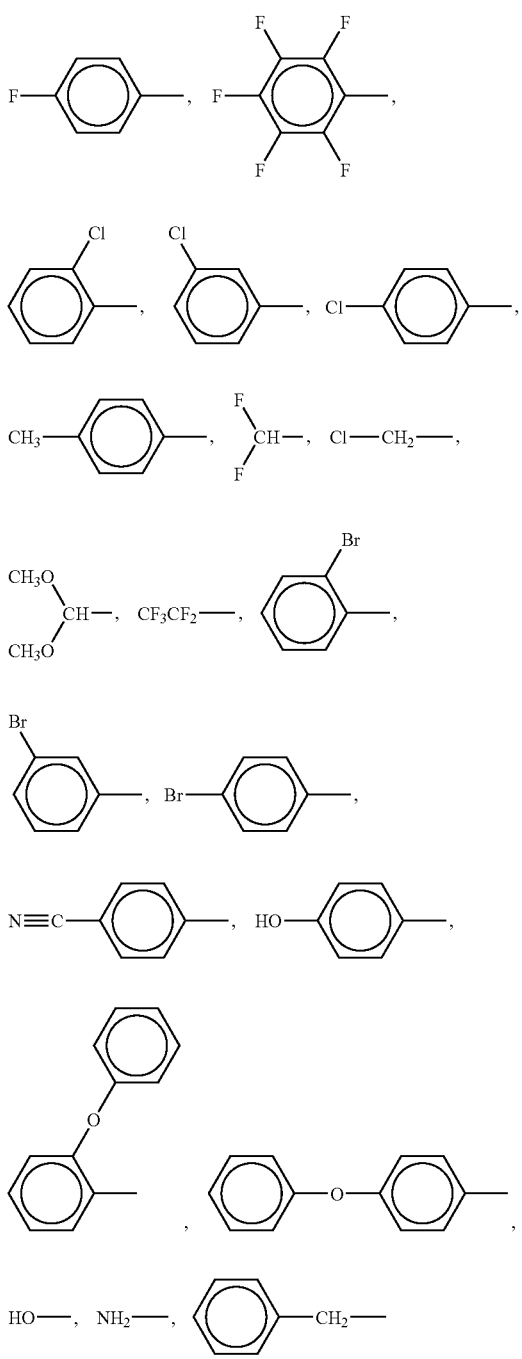

[Chemical Formula 13]
<Specific Examples of X>

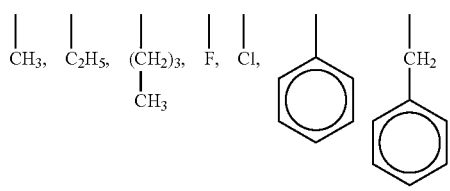

There are no limitations regarding the method for producing the silver β-ketocarboxylate, as long as it is possible to produce compounds like those discussed above, and a specific example is the method of producing a silver β-ketocarboxylate of the invention. The silver β-ketocarboxylates discussed above are novel compounds, and their method of production was established by the present inventors after intensive investigation, making their production possible for the first time.

The method of producing a silver β-ketocarboxylate of the invention is a method of producing a silver β-ketocarboxylate that includes the step of producing a silver β-ketocarboxylate by reacting a β-ketocarboxylic acid and a silver compound in a reaction liquid whose water content is 55 wt % or less. An example of the production method of the invention is described below, but there is no limitation to this.

First, a β-ketocarboxylate salt is prepared. This β-ketocarboxylate salt can for example be created by hydrolysis of a β-ketocarboxylate ester. For hydrolysis of an ester, normally a base is used, and there are no limitations regarding the base and possible examples include NaOH and KOH. The base can be prepared as an aqueous solution, and its concentration is for example 1 mol/L or more, and preferably 2 to 5 mol/L.

Specifically, it is for example possible to add a β-ketocarboxylate ester dropwise to an aqueous solution of the base while stirring, reacting them. There are no particular limitations regarding the proportion at which the base is added, and preferably 0.8 to 2 mol, and more preferably 0.9 to 1.2 mol, are added per 1 mol β-ketocarboxylate ester. The concentration of the β-ketocarboxylate ester in the reaction liquid is for example 0.5 to 6.25 mol/L, and preferably 1 to 5.6 mol/L. There are no particular limitations regarding the reaction temperature, and for example preferably it is not more than 50° C., more preferably not more than 40° C., and particularly preferably 20 to 40° C. The reaction time is for example 0.5 to 48 hours, and preferably 1 to 4 hours.

It should be noted that in this step, to sufficiently reduce the amount of residual base (NaOH, etc.) in the reaction solution after the reaction is over, it is preferable that the amount of base that is used is set lower than the amount of β-ketocarboxylate ester that is used, and for example, preferably it is set to 0.8 to 1 mol, and more preferably 0.8 to 0.9 mol, per 1 mol β-ketocarboxylate ester. This condition is preferable when the β-ketocarboxylate salt is isolated and afterwards supplied to the next step. On the other hand, when the β-ketocarboxylate salt that is produced in this step is to be supplied for the next step as is, then, for example, 1 to 1.3 mol (preferably 1.1 to 1.2 mol) of base is added per 1 mol β-ketocarboxylate ester to produce the β-ketocarboxylate salt. Then, in the next step it is sufficient to add an amount of acid (sulfuric acid, etc., as discussed later) that is equivalent to the amount of base that has been used.

There are no particular limitations regarding the β-ketocarboxylate ester, and it can be set suitably according to the structure of the desired silver β-ketocarboxylate. For example, a β-ketocarboxylate ester is represented by Formula (2) below, and in Formula (2), R and X are the same as in Formula (1) and there are no particular limitations regarding R', and examples thereof include methyl, ethyl, isopropyl, and benzyl. Examples of specific compounds include methyl isobutyrylacetate, ethyl benzoylacetate, methyl acetoacetate, methyl propionylacetate, benzyl isobutyrylacetate, isopropyl isobutyrylacetate, ethyl 2-methylacetoacetate, ethyl 2-ethylacetoacetate, and ethyl 2-n-butylacetate.

[Chemical Formula 14]

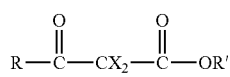

(2)

The raw material is not limited to such β-ketocarboxylate esters, and for example, it is possible to use a cyclic compound that becomes an ester upon ring opening. Such cyclic compounds that may be used include the following compounds.

[Chemical Formula 15]

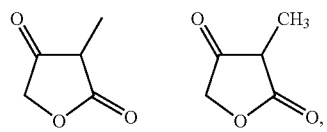

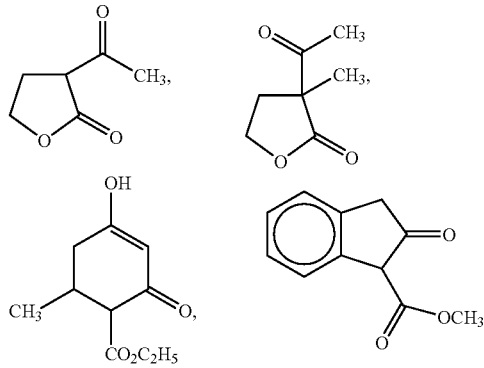

The β-ketocarboxylate salt that is obtained is represented by Formula (3). In Formula (3), R and X are the same as in Formula (1). R" is not particularly limited, and it is determined based on the type of salt that is used, and for example it may be Na, K, or NH₄, for example. Specific examples of compounds include Na or K isobutyrylacetate, Na or K benzoylacetate, Na or K acetoacetate, Na or K propionylacetate, Na or K isobutyrylacetate, Na or K 2-methylacetoacetate, Na or K 2-ethyl acetoacetate, and Na or K 2-butylacetoacetate.

[Chemical Formula 16]

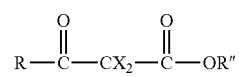

(3)

As discussed before, this β-ketocarboxylate salt can be prepared by hydrolysis of an β-ketocarboxylate ester, and it is possible to isolate the β-ketocarboxylate salt that is obtained with an ordinary method and then use its hydrolysate as is when mixing with the silver compound in the next step.

Next, the β-ketocarboxylate salt and the silver compound are mixed to produce the silver β-ketocarboxylate. A first method and a second method for producing the silver β-ketocarboxylate are illustrated below.

First, acid is added to a β-ketocarboxylate salt represented in Formula (3), and the β-ketocarboxylic acid that is produced is extracted with an organic solvent. There are no particular limitations regarding the acid, and for example it is possible to use sulfuric acid, hydrochloric acid, HBr, nitric acid, phosphoric acid, or acetic acid. There is no particular limitation with regard to the amount of acid that is used, and for example, it is sufficient to supply an amount of hydrogen that corresponds to the R" of the β-ketocarboxylate salt that is represented by Formula (3). If the β-ketocarboxylate salt that is produced in the previous step is used as is without being isolated, then it is sufficient to have an amount of acid that can supply an amount of hydrogen that corresponds to the base that is used in the previous step. By extracting with an organic solvent in this way, the purity of the silver β-ketocarboxylate that is obtained can be increased even further. The β-ketocarboxylic acid that is obtained in this step is preferably quickly cooled with ice, for example, after it is produced, before advancing to the next step.

Next, the silver compound is added to the β-ketocarboxylic acid to create the silver β-ketocarboxylate.

The reaction between these two ordinarily is carried out in solvent, and in order to produce silver β-ketocarboxylate efficiently, it is preferable that the water content of the reaction solution is reduced. In other words, as the water content of the reaction solution is lowered, the productivity of silver β-ketocarboxylate is increased in relative terms. Specifically, the proportion (wt %) of water in the reaction solution is for example 55 wt % or less, preferably 50 wt % or less, and more preferably 44 wt % or less. There is no particular limitation regarding the lower limit, and for example it may be about 35 wt %, and particularly preferably is below the detectable limit. The solvent of the reaction solution is for example an organic solvent such as ether, water, or a mixture of these.

The ratio at which the β-ketocarboxylic acid and the silver compound are blended is not particularly limited, and preferably 1 to 1.5 mol β-ketocarboxylic acid is blended per 1 mol silver compound, and more preferably 1 to 1.2 mol β-ketocarboxylic acid is blended per 1 mol silver compound. It is sufficient to use at least one each of the β-ketocarboxylic acid and the silver compound, but it is also possible to use two or more types of each together.

β-ketocarboxylic acid ordinarily is used as a β-ketocarboxylic acid solution in which it is dissolved or dispersed in an organic solvent. There are no particular limitations regarding the organic solvent, and examples include esters such as ethyl acetate and ethers such as diethyl ether. There are no particular limitations regarding the concentration of the β-ketocarboxylic acid solution, and it may be 0.2 mol/L or more and preferably is 0.5 mol/L or more.

The silver compound ordinarily is added as a silver compound solution (such as a silver compound aqueous solution), but, as mentioned before, in order to lower the water content of the reaction solution, the concentration of the silver compound is for example 1 mol/L or more, preferably 2 mol/L or more, and more preferably 3 mol/L, and there is no particular limitation regarding its upper limit, and for example this may be 13 mol/L or less. If the a position of the silver β-ketocarboxylate that is produced is not to be substituted, then the concentration of the silver compound solution is for example 1 mol/L or more, preferably 1.5 mol/L or more, and more preferably 2 mol/L or more, and if its a position is to be substituted, then the concentration of the silver compound solution is for example 3 mol/L or more, preferably 4 mol/L or more, and more preferably 5 mol/L or more. Specifically, in the case of silver acetoacetate, the concentration is for example 3 mol/L or more, preferably 4 mol/L or more, and more preferably 5 mol/L or more.

There are no particular limitations regarding the silver compound, and possible examples include silver nitrate, silver chloride, silver carbonate, silver bromide, and silver iodide, and of these, silver nitrate is particularly preferable because of its relatively high water solubility, stability and safety. In the reaction between the β-ketocarboxylic acid and the silver compound, to dissociate the —COOH group of the β-ketocarboxylic acid to a carboxylate (—COO—), it is for example possible to add an amine such as diethanolamine, methylaminoethanol, dimethylaminoethanol, or triethanolamine. There are no restrictions regarding the proportion of amine that is added, and for example, it is added at 1 to 1.5 mol per 1 mol silver compound, and preferably at 1 to 1.1 mol per 1 mol silver compound. Adding an amine causes the β-ketocarboxylic acid to move from the organic phase to the aqueous phase, for example. Thus, if an amine is to be added, then it is not particularly necessary to consider the concentration of β-ketocarboxylic acid in the β-ketocarboxylic acid solution (organic solution). It is also possible to add amine to transfer the β-ketocarboxylic acid from the organic phase to the aqueous phase, then separate off only the aqueous phase at this point and mix the β-ketocarboxylic acid aqueous solution (aqueous phase) with the silver compound solution (such as a silver compound aqueous solution) in order to create the silver β-ketocarboxylate.

The amine is ordinarily added as an amine solution (such as an aqueous amine solution), but as discussed earlier, in order to lower the water content of the reaction solution, the concentration of the amine solution is for example 2 mol/L or more, preferably 4 mol/L or more, and more preferably 6 mol/L or more. There is no particular restriction regarding its upper limit, and for example, this is 8 mol/L or less.

The β-ketocarboxylic acid concentration in the reaction solution is for example 0.1 to 5 mol/L, and preferably 0.3 to 3 mol/L. The amine concentration in the reaction solution is for example 0.1 to 5 mol/L, and preferably 0.3 to 3 mol/L. If the silver β-ketocarboxylate that is produced is to have an unsubstituted a position, then the silver compound concentration in the reaction solution is for example 0.1 mol/L, preferably 0.3 mol/L, and more preferably 0.5 mol/L or more, and if its a position is substituted, then the concentration of the silver compound solution is for example 0.1 mol/L, preferably 0.5 mol/L, and more preferably 2 mol/L or more. Specifically, in the case of silver acetoacetate, the concentration of the silver compound solution is for example 0.1 mol/L, preferably 0.5 mol/L, and more preferably 2 mol/L or more, and in the case of silver isobutyrylacetate, the concentration is for example 0.15 mol/L, preferably 0.4 mol/L, and more preferably 0.6 mol/L.

There are no particular restrictions regarding the conditions of the reaction between the β-ketocarboxylic acid and the silver compound, and for example, preferably the reaction time is 0.1 to 0.5 hours and the reaction temperature is 0 to 25° C.

The silver β-ketocarboxylate that is obtained in this way is for example quickly recovered and dried following the reaction, and then used as is as a material for forming metal silver, but preferably it is purified before use by washing with water or alcohol such as ethanol.

It should be noted that in addition to the above method, there is for example also the method of producing silver β-ketocarboxylate by directly adding a silver compound to a β-ketocarboxylate salt. In this case, it is preferable that a β-ketocarboxylate salt solution (such as an aqueous solution) is added to a silver compound solution (such as an aqueous silver compound solution).

The material for forming metal silver of the invention also can be a dispersion or a solution in which the silver β-ketocarboxylate is dispersed or dissolved in a medium.

There are no particular restrictions regarding medium type, but preferably the medium is evaporated away when the material for forming metal silver is heated, and for example it may be an alcohol such as isopropanol, butoxyethanol, methoxyethanol, and ethoxyethanol, an ether such as acetoxymethoxypropane, phenyl glycidyl ether, and ethylene glycol glycidyl, sulfoxides such as DMSO, as well as water and 1-methyl-2-pyrrolidone.

The material for forming metal silver of the invention also can include components other than silver β-ketocarboxylate, as long as they do not adversely impact the effect of the invention. Examples of components include epoxy resin, phenolic resin, polyester resin, and hardening agent.

The forming material of the invention can be used in combination with a metal silver forming material conventionally known to the public, such as inorganic material like silver oxide and organic material such as silver behenate and silver α-ketocarboxylate. This combination with silver β-ketocarboxylate makes it possible to enhance the characteristics of conventionally known forming material (such as its usability)

and the characteristics of the metal silver that it forms (such as to increase the conductivity and lower the resistance).

Next, as discussed earlier, the method of producing the metal silver of the invention is characterized in that it includes a step of heating the metal silver forming material, and the forming material is forming material that includes the silver β-ketocarboxylate of the invention.

In the production method of the invention, there are no particular limitations regarding the temperature at which the forming material is heated, but because a silver β-ketocarboxylate like those described earlier is used, the heating temperature can be set to within a range of approximately 60 to 210° C. The heating temperature can be set in accordance with the decomposition temperature of the silver β-ketocarboxylate, and for example, it can be the same or higher than the decomposition temperature. For example, a range of +0 to +20° C. with respect to the decomposition temperature is preferable, and a range of +0 to +10° C. with respect to the decomposition temperature is more preferable. By setting the heating temperature to within this range, it becomes possible to advance the decomposition of the silver β-ketocarboxylate more reliably.

Specifically, if the silver β-ketocarboxylate is silver isobutyrylacetate (decomposition temperature approximately 145° C.), for example, then the heating temperature preferably is in the range of 145 to 165° C., more preferably in the range of 145 to 155° C., and even more preferably in the range of 145 to 150° C., and if the silver β-ketocarboxylate is silver benzoylacetate (decomposition temperature approximately 120° C.), then the heating temperature is preferably in the range of 120 to 140° C., and more preferably in the range of 120 to 130° C. If the silver β-ketocarboxylate is silver acetoacetate (decomposition temperature approximately 110° C.), then the heating temperature is preferably in the range of 110 to 130° C., and more preferably in the range of 110 to 120° C., and if the silver β-ketocarboxylate is silver propionylacetate (decomposition temperature approximately 130° C.), then the heating temperature is preferably in the range of 130 to 150° C., more preferably in the range of 130 to 140° C., and even more preferably in the range of 130 to 135° C. If the silver β-ketocarboxylate is silver α-methylacetoacetate (decomposition temperature approximately 95° C.), then the heating temperature is preferably in the range of 90 to 120° C., more preferably in the range of 90 to 110° C., and even more preferably in the range of 90 to 100° C. If the silver β-ketocarboxylate is silver α-ethylacetoacetate (decomposition temperature approximately 100° C.), then the heating temperature is preferably in the range of 95 to 120° C., more preferably in the range of 95 to 110° C., and even more preferably in the range of 95 to 100° C.

The metal silver production method of the invention will be described using the formation of a metal silver film on a base material as an example. It should be noted that it is only necessary for the production method of the invention to use the forming material of the invention, and it is not limited whatsoever to the method below.

First, a dispersion or a solution in which the silver β-ketocarboxylate is dispersed or dissolved in a medium is prepared, and this is taken as the forming material. There are no particular limitations regarding the medium, and a medium such as those described previously can be used.

There is no particular restriction regarding the concentration of the silver β-ketocarboxylate in the forming material, and it can be chosen suitably based on the handleability (ease of application, etc.) or the desired thickness of the metal silver film, and for example it is 0.5 to 5 mol/L and preferably 0.5 to 3 mol/L.

Next, this forming material is applied onto the base material. The base material is not particularly limited and can be chosen suitably in accordance with the application of the metal silver film that is formed, and possible examples include glass, ceramic, polyimide, polyethylene terephthalate, and epoxy resin. In particular, the metal silver production method of the invention allows for the use of lower heat-resistant base materials than conventional production methods, which require high temperature processing, and thus base materials made of resin, such as polyethylene terephthalate and epoxy resin, become possibilities as well. Examples of methods for applying the forming material include screen printing, offset printing, dipping, ink-jet printing, and dispensing. There is no particular restriction regarding the amount of forming material that is applied per area of base material, and for example, it can be suitably chosen based on the concentration of the silver β-ketocarboxylate in the forming material or the thickness of the metal silver film to be formed.

Heating of the forming material can be carried out by a method such as electric furnace heating or with a thermosensitive heat head, and there are no particular restrictions regarding the heating conditions, and for example, heating can be carried out at atmospheric pressure.

In this way the metal silver film can be formed on the base material. As discussed earlier, the silver β-ketocarboxylate of the invention is decomposed rapidly and sufficiently at the decomposition temperature, and thus the metal silver film that is formed also can attain excellent conductivity, that is, a low resistance. Specifically, the resistance of the metal silver can be set to approximately $1 \times 10^{-3}$ to $1 \times 10^{-5}$ Ωcm. This resistance is a sufficiently practical value, and in particular, because a resistance on the order of $1 \times 10^{-5}$ Ωcm is excellent, the metal silver that is formed by the production method of the invention can be considered extremely useful as a conductive material.

There is no limitation to the application of the metal silver that is formed by the production method of the invention as a conductive material, and examples of applications include connection wiring, electrodes, and conductive adhesives. In particular, the silver β-ketocarboxylate is an organic compound, and readily blends with solvent or the like and allows the viscosity, for example, of the forming material of the invention to be adjusted easily, and thus the production method of the invention in particular allows fine connection wiring, for example, to be formed with ease.

It is further preferable for the metal silver forming material of the invention to be blended with a resin that confers properties to the metal silver such as conductivity, antibacterial activity, and electrostatic properties. As mentioned before, the silver β-ketocarboxylate of the invention is an organic material and readily blends with resin, for example, and can be decomposed near the curing temperature of the resin, and thus if it is blended with resin and processed at a predetermined temperature (such as the resin curing temperature) and then molding is performed, it is possible to produce a metal silver from the silver β-ketocarboxylate at the same time as molding. The properties of the metal silver therefore readily can be added to the resin mold, for example. It should be noted that the processing temperature can be suitably chosen based on the curing temperature of the resin and the decomposition temperature of the silver β-ketocarboxylate.

Working Example 1

Synthesis of Silver Isobutyrylacetate

Sodium hydroxide (0.4 g) was dissolved in water (10 mL), and methyl isobutyrylacetate (1.44 g: made by Fluka) was added and this was agitated for six hours at room temperature.

The reaction product was washed with ether, then 10% dilute sulfuric acid (4.9 g) was added and the mixture was extracted with ether. The ether extract was dried by adding excess anhydrous sodium sulfate, and the anhydrous sodium sulfate was removed by filtration. The ether was then removed with a rotary evaporator, yielding isobutyrylacetic acid (yield 1 g).

Diethanolamine (0.33 g) was dissolved in water (5 mL), and to this was added an ether solution (10 mL) containing isobutyrylacetic acid (0.43 g). Next, the mixture was stirred at 15° C. while an aqueous solution (5 mL) containing silver nitrate (0.51 g) was added dropwise, and this further was stirred for 15 minutes. The white precipitate that settled was filtered off to obtain silver isobutyrylacetate (yield 0.37 g). FIG. 1 shows the infrared absorption spectrum (IR) of the silver isobutyrylacetate that was obtained. IR:1709 $cm^{-1}$, 1505 $cm^{-1}$.

The NMR (in deuterated DMSO) of the silver isobutyrylacetate that was obtained is shown below.

| 1.00 ppm 6H d | |
|---|---|
| 2.83 ppm 1H quintet | |
| 3.30 ppm 2H s | J = 7 Hz |
| | elemental analysis |
| measured values | C 30.33 H 3.65 N 0.00 Ag 45.42 |
| calculated values | C 30.41 H 3.84 Ag 45.51 |

Working Example 2

Synthesis of Silver Acetoacetate

Figure 2:
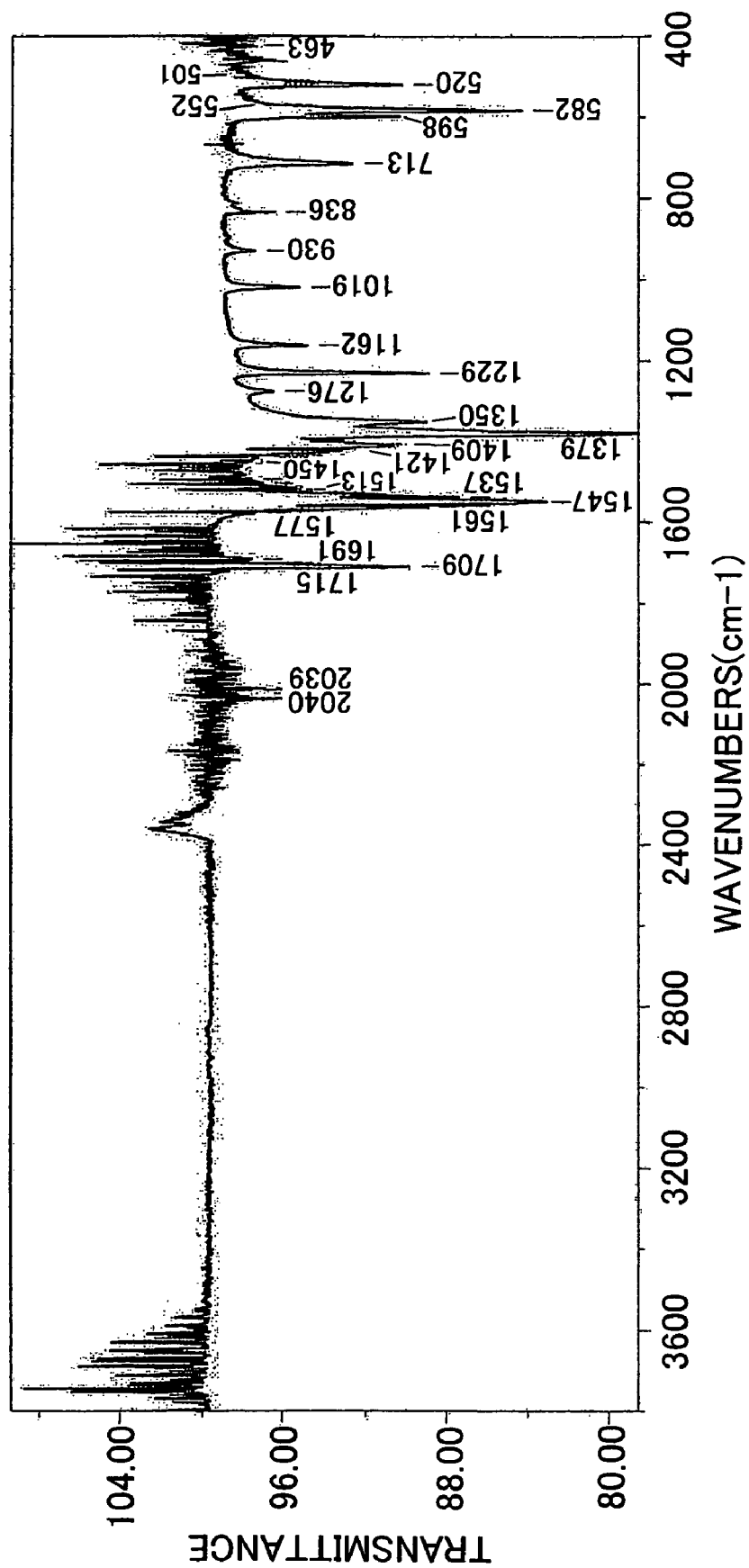
FIG. 2 is a graph showing the infrared absorption spectrum of silver acetoacetate in another example of the invention.

Sodium hydroxide (0.8 g) was dissolved in water (10 mL), and methyl acetoacetate (2.2 g: made by Wako Pure Chemical Industries) was added and this was stirred overnight at room temperature. Silver nitrate (3.4 g) was then added, and this was agitated for 15 minutes at 15° C. The precipitate that settled was filtered off to obtain silver acetoacetate (yield 3.52 g). FIG. 2 shows the infrared absorption spectrum (IR) of the silver acetoacetate that was obtained. IR:1709 $cm^{-1}$, 1547 $cm^{-1}$.

The NMR (in deuterated DMSO) of the silver acetoacetate that was obtained is shown below.
2.17 ppm 3H s
3.25 ppm 2H s Working Example 3

Synthesis of Silver Propionylacetate

Sodium hydroxide (0.4 g) was dissolved in water (10 mL), and methyl propionylacetate (1.3 g: made by Aldrich) was added and this was agitated for three hours at room temperature. The reaction product was washed with ether, then 10% dilute sulfuric acid (4.9 g) was added and the product was extracted with ether. The ether extract was dried by adding excess anhydrous sodium sulfate, and the anhydrous sodium sulfate was removed by filtration. The ether was then removed with a rotary evaporator, yielding propionylacetic acid (yield 0.88 g).

Figure 3:
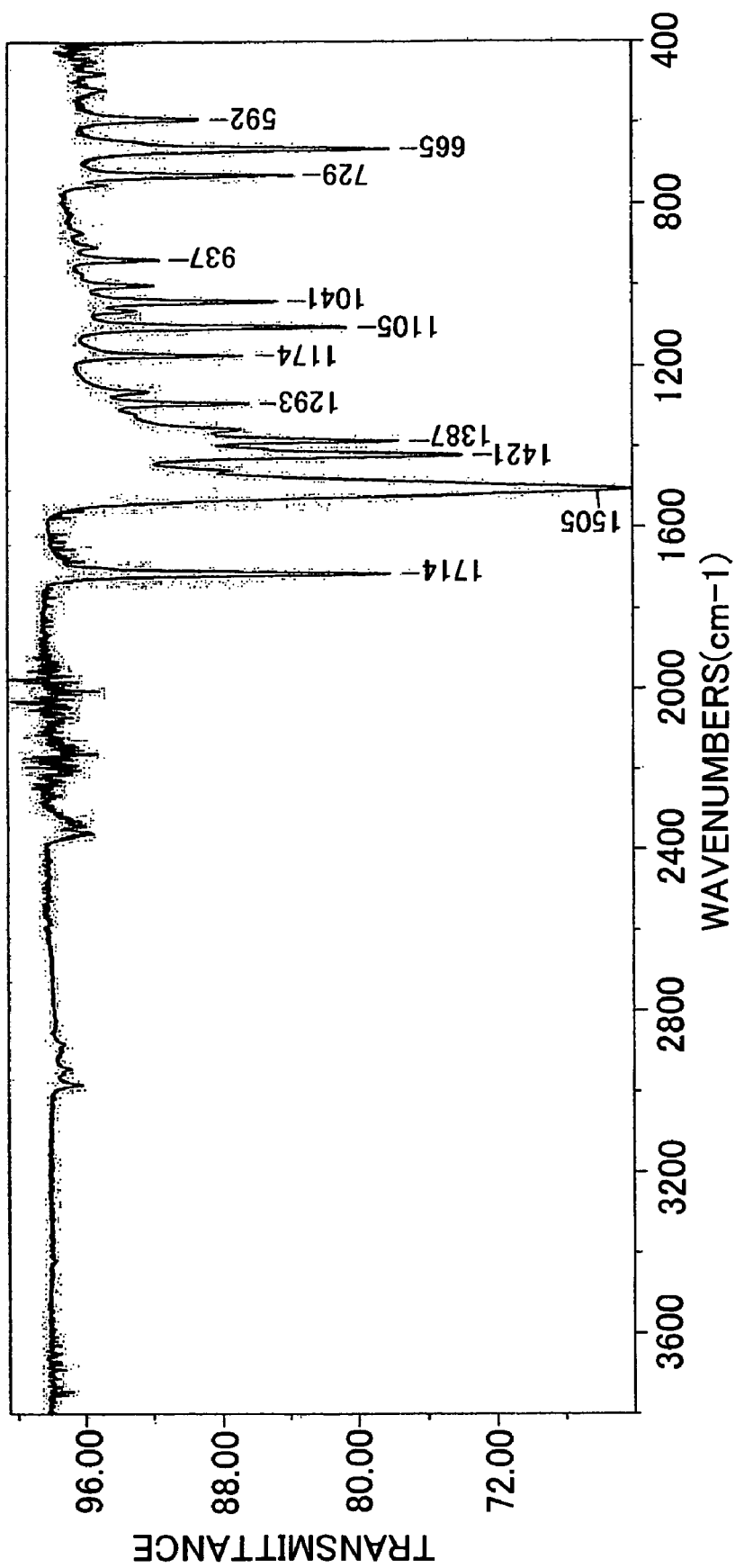
FIG. 3 is a graph showing the infrared absorption spectrum of silver propionylacetate in a yet further example of the invention.

Diethanolamine (0.22 g) was dissolved in water (0.5 mL), and to this was added an ether solution (3 mL) containing propionylacetic acid (0.25 g). Next, the mixture was stirred at 15° C. while an aqueous solution (1 mL) containing silver nitrate (0.34 g) was added dropwise, and this was further stirred for 15 minutes. The white precipitate that settled was filtered off to obtain silver propionylacetate (yield 1.89 g). FIG. 3 shows the infrared absorption spectrum (IR) of the silver propionylacetate that was obtained. IR:1714 $cm^{-1}$, 1505 $cm^{-1}$.

The NMR (in deuterated DMSO) of the silver propionylacetate that was obtained is shown below.

| 0.87 ppm 3H t | |
|---|---|
| 2.55 ppm 2H q | |
| 3.25 ppm 2H s | J = 7 Hz |

Working Example 4

Synthesis of Silver Benzoylacetate

Sodium hydroxide (0.4 g) was dissolved in water (10 mL), and ethyl benzoylacetate (2.14 g: 90% pure, made by Aldrich) was added and this was agitated overnight at room temperature. The reaction product was washed with ether, then 10% dilute sulfuric acid (4.9 g) was added and the reaction product was extracted with ether. The ether extract was dried by adding excess anhydrous sodium sulfate, and the anhydrous sodium sulfate was removed by filtration. The ether was then removed with a rotary evaporator, yielding benzoylacetic acid (yield 1.05 g).

Figure 4:
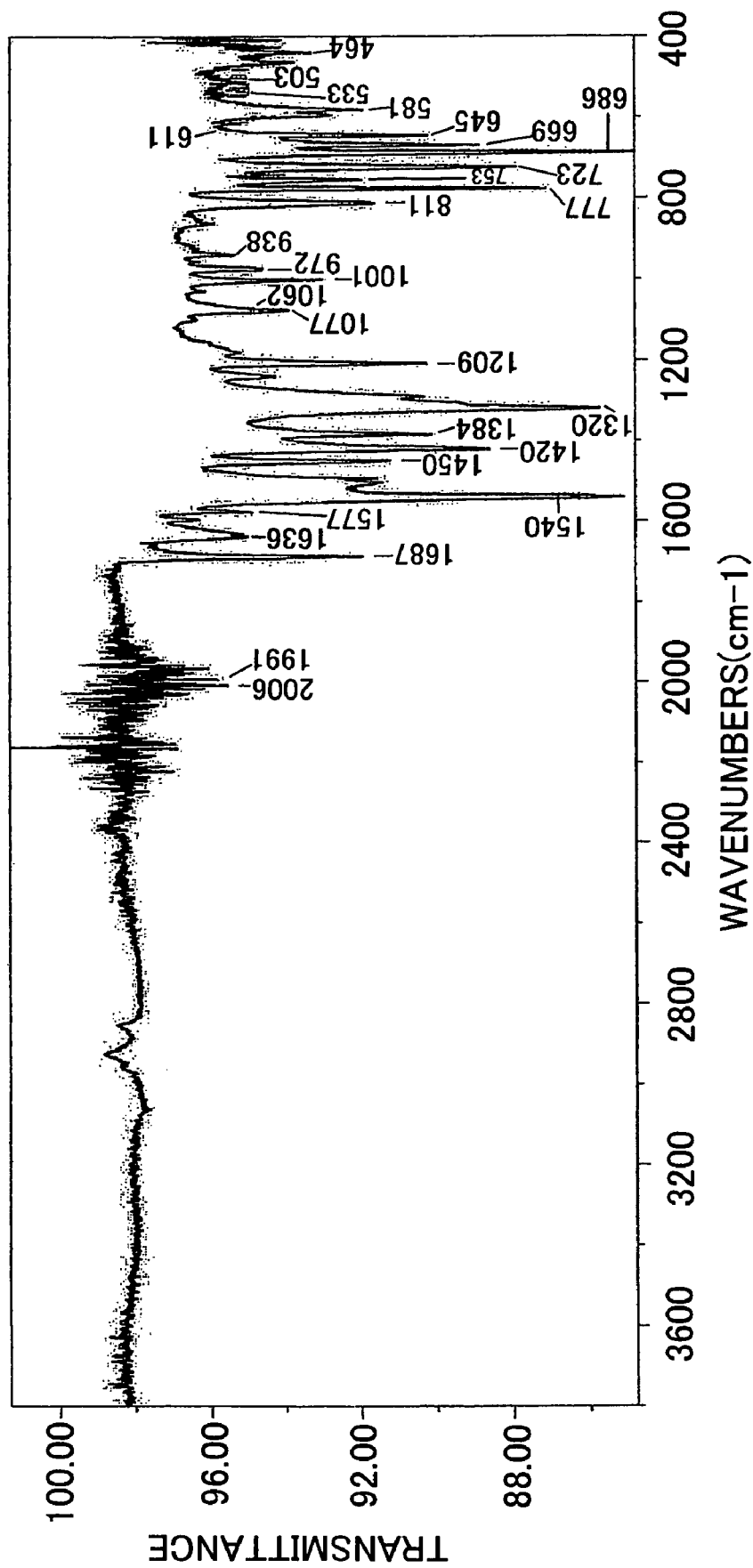
FIG. 4 is a graph showing the infrared absorption spectrum of silver benzoylacetate in a yet further example of the invention.

Diethanolamine (0.33 g) was dissolved in water (5 mL), and to this was added an ether solution (20 mL) containing benzoylacetic acid (0.54 g). Next, the mixture was stirred at 15° C. while an aqueous solution (5 mL) containing silver nitrate (0.51 g) was added dropwise, and this further was stirred for 15 minutes. The pale yellow precipitate that settled was filtered off, yielding silver benzoylacetate (yield 0.79 g). FIG. 4 shows the infrared absorption spectrum (IR) of the silver benzoylacetate that was obtained. IR:1687 $cm^{-1}$, 1540 $cm^{-1}$.

The NMR (in deuterated DMSO) of the silver benzoylacetate that was obtained is shown below.
3.55 ppm 2H s
7.45 to 8.00 ppm 5H m Working Example 5

Synthesis of Silver α-Methylacetoacetate

Sodium hydroxide (1.92 g) was dissolved in water (8 mL) and ethyl 2-methylacetoacetate (5.77 g: made by Wako Pure Chemical Industries) was added while stirring at room temperature, and this was stirred for another 30 minutes. The ethanol subsequently was removed with a rotary evaporator, and the remaining aqueous layer was washed with ether. To this was added ether (20 mL), and then, while stirring and chilling on ice, a solution of concentrated sulfuric acid 2.35 g dissolved in water 8 mL was added dropwise. The ether layer was fractioned off, and the aqueous layer was salt precipitated and then extracted with ether. The ether layers were combined to yield an ether solution of α-methylacetoacetic acid.

Diethanolamine (4.4 g) was dissolved in water (5 mL), and this solution was added to the ether solution of α-methylacetoacetic acid while cooling with ice. A solution of silver nitrate (6.8 g) dissolved in water (8 mL) was then added dropwise. The white precipitate that precipitated was filtered off, washed with ice water and then isopropanol, and then dried, yielding silver α-methylacetoacetate as a white precipitate (yield 4.78 g).

Figure 5:
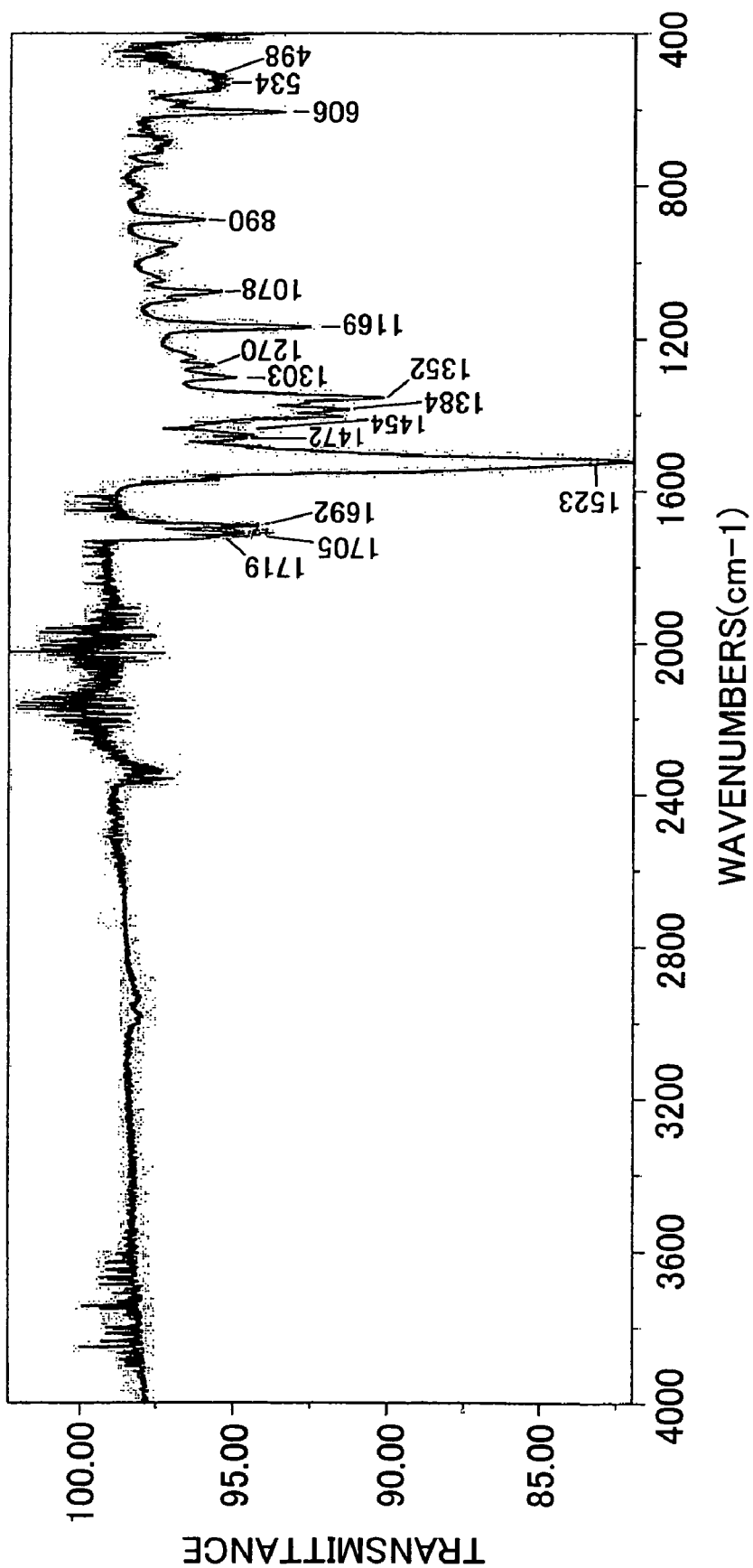
FIG. 5 is a graph showing the infrared absorption spectrum of silver α-methyl acetoacetate in a yet further example of the invention.

FIG. 5 shows the infrared absorption spectrum (IR) of the silver α-methylacetoacetate that was obtained. IR:1692 cm$^{-1}$, 1523 cm$^{-1}$.

elemental analysis: C=26.49%, H=3.11%, Ag=48.91%

(theoretical values: C=26.93%, H=3.16%, Ag=48.36%)

The NMR (in deuterated DMSO) of the silver α-methylacetoacetate that was obtained is shown below.

| | |
|---|---|
| 1.25 ppm 3H d | |
| 2.25 ppm 3H s | |
| 3.55 ppm 1H q | J = 7 Hz |

Working Example 6

Synthesis of Silver α-Ethylacetoacetate

Sodium hydroxide (1.92 g) was dissolved in water (10 mL) and ethyl 2-ethylacetoacetate (6.32 g: made by Wako Pure Chemical Industries) was added while stirring at room temperature, and this was further stirred for 30 minutes. The ethanol was subsequently removed with a rotary evaporator, and the remaining aqueous layer was washed with ether. To this was added ether (20 mL), and then, while stirring and chilling with ice, a solution of concentrated sulfuric acid 2.35 g dissolved in water 8 mL was added dropwise. The ether layer was fractioned off, and the aqueous layer was salt precipitated and extracted with ether. The ether layers were combined to yield an ether solution of α-ethylacetoacetic acid.

Figure 6:
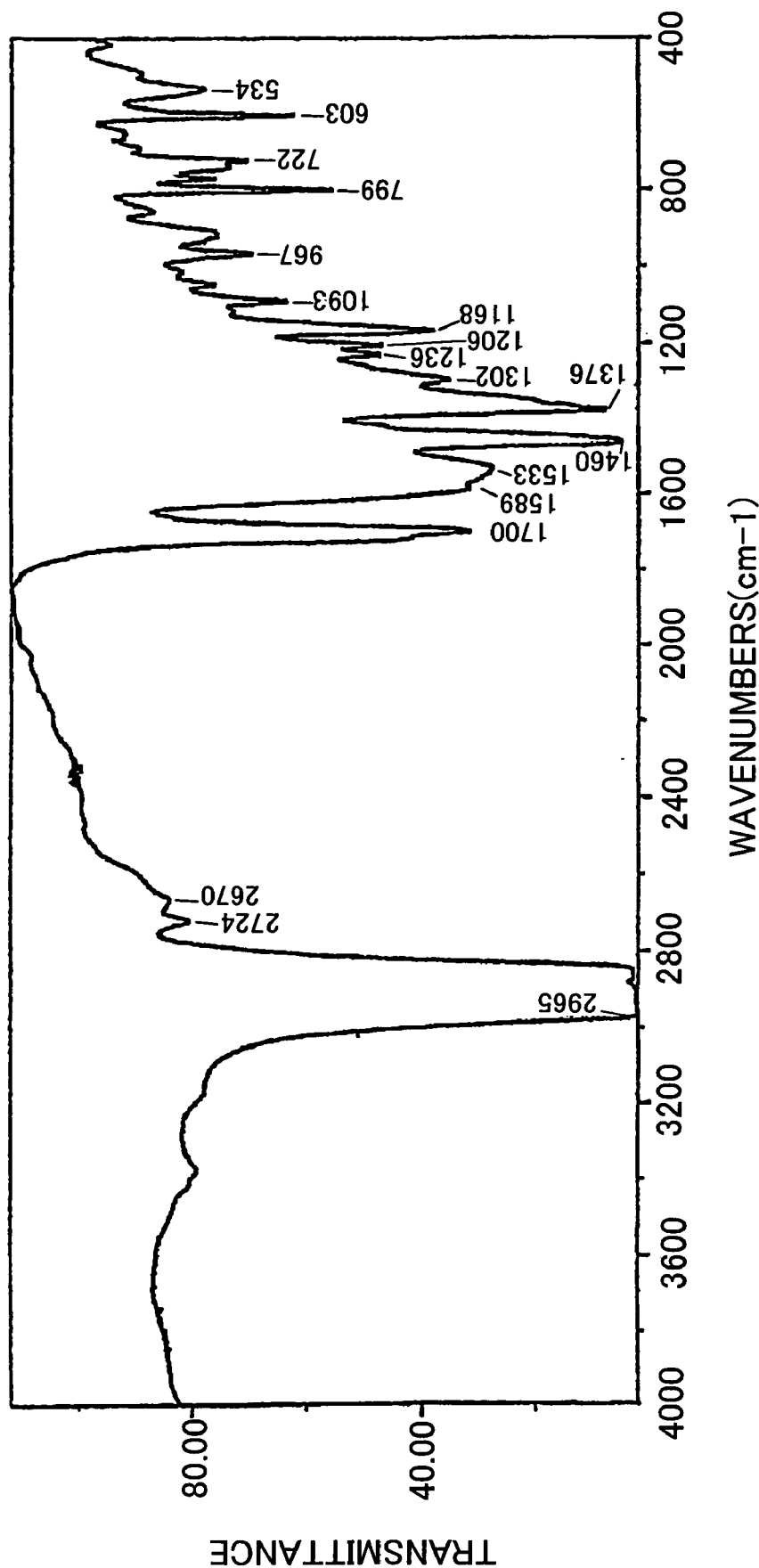
FIG. 6 is a graph showing the infrared absorption spectrum of silver α-ethyl acetoacetate in a yet further example of the invention.
Figure 7:
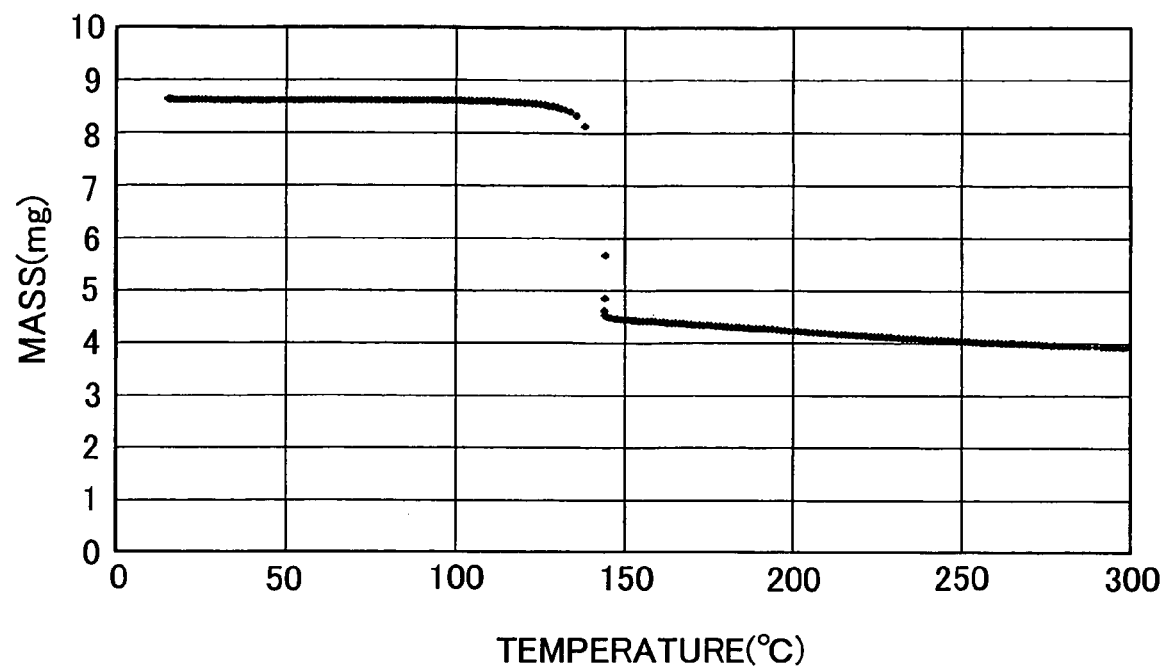
FIG. 7 is a graph that shows the measurement results of the thermogravimetric analysis of silver isobutyrylacetate in a yet further example of the invention.
Figure 8:
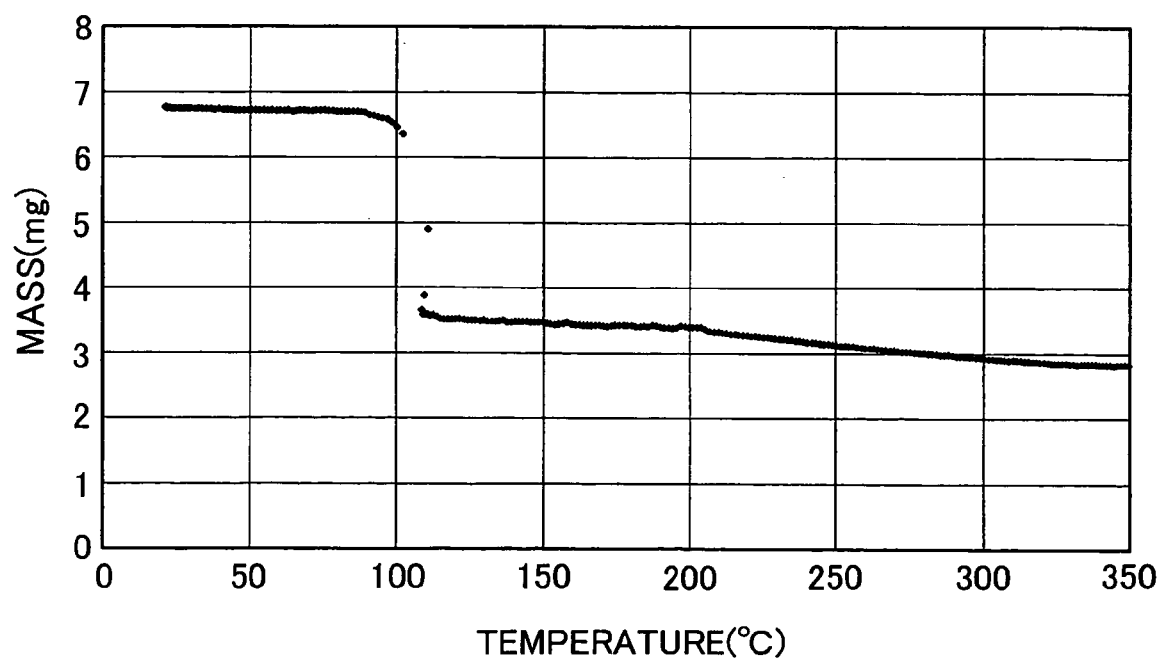
FIG. 8 is a graph that shows the measurement results of the thermogravimetric analysis of silver acetoacetate in a yet further example of the invention.
Figure 9:
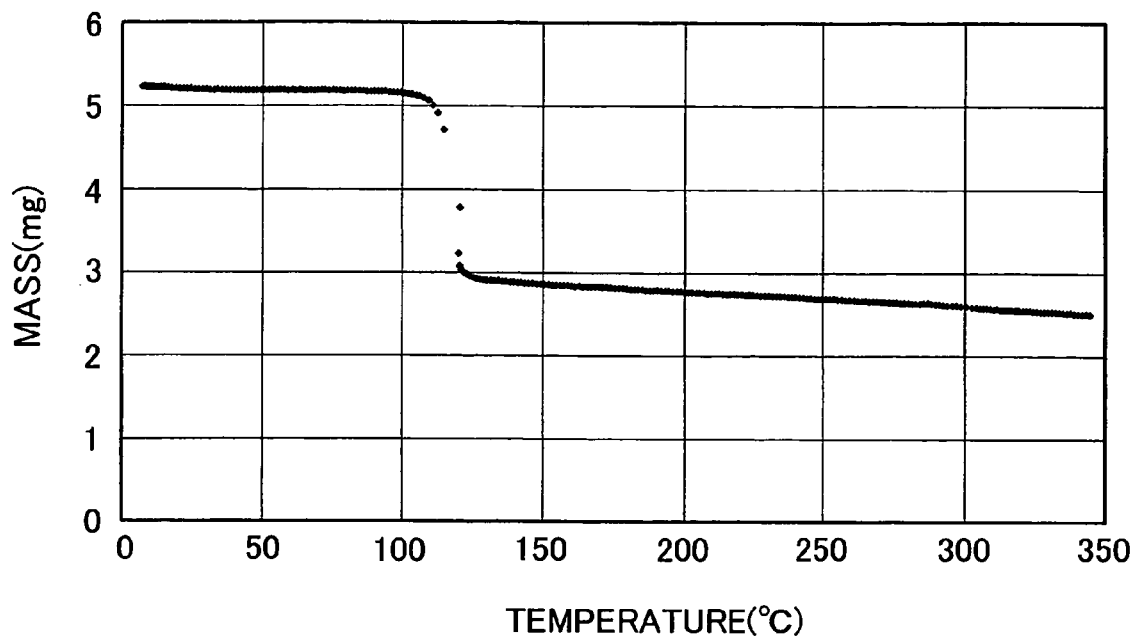
FIG. 9 is a graph that shows the measurement results of the thermogravimetric analysis of silver propionylacetate in a yet further example of the invention.
Figure 10:
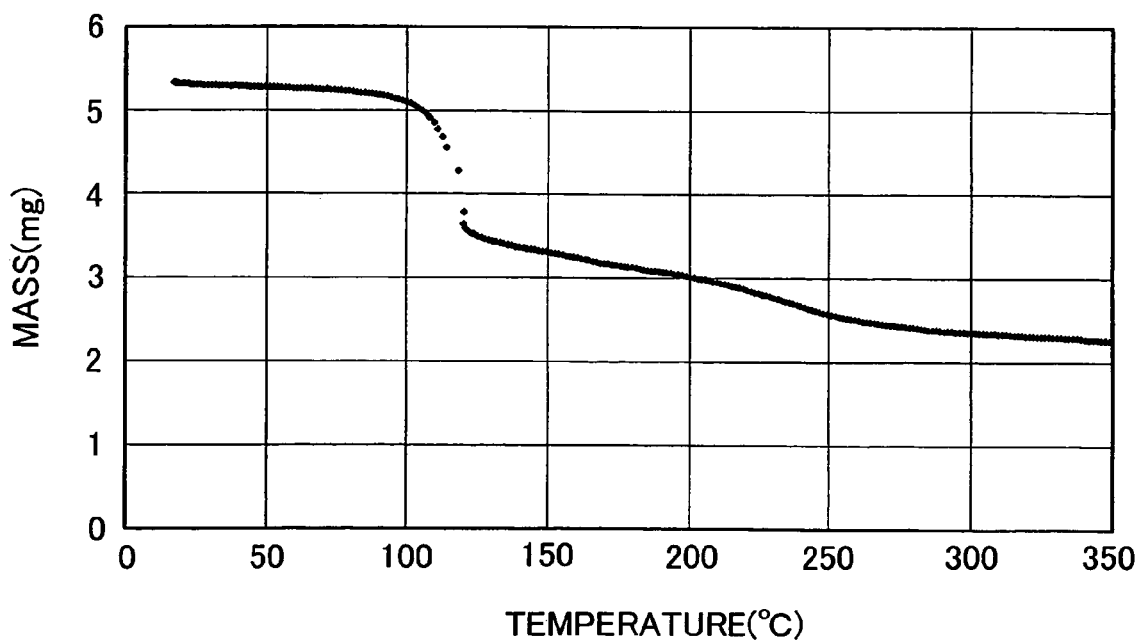
FIG. 10 is a graph that shows the measurement results of the thermogravimetric analysis of silver benzoylacetate in a yet further example of the invention.
Figure 11:
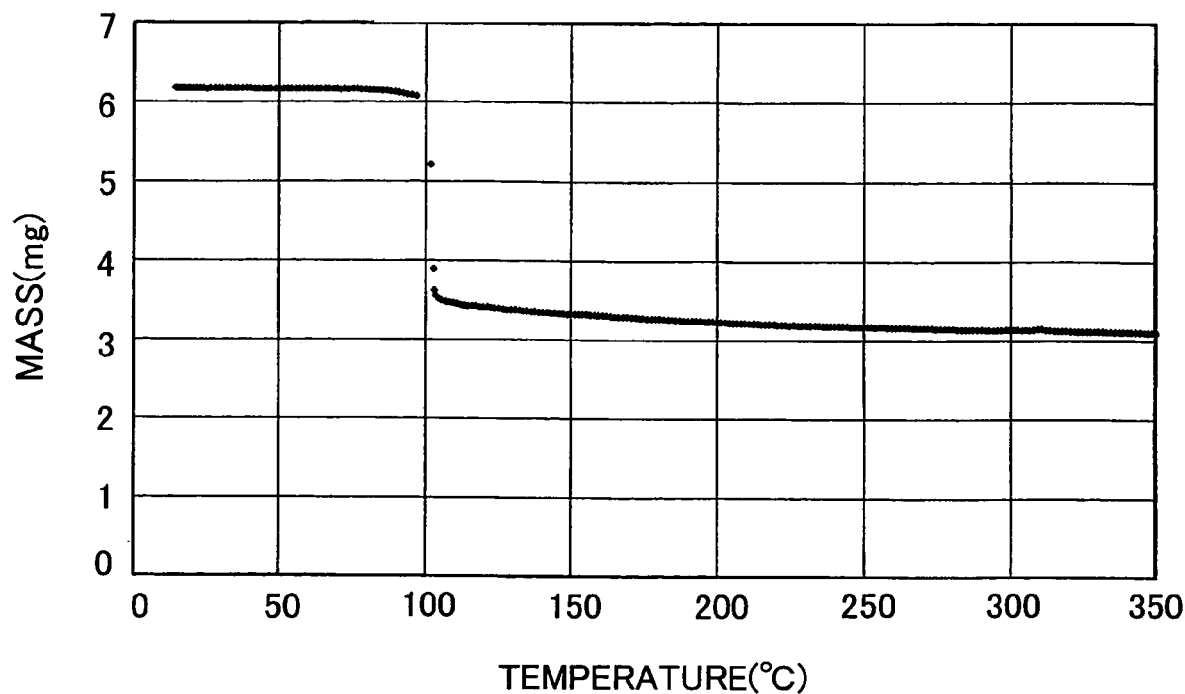
FIG. 11 is a graph that shows the measurement results of the thermogravimetric analysis of silver α-methyl acetoacetate in a yet further example of the invention.
Figure 12:
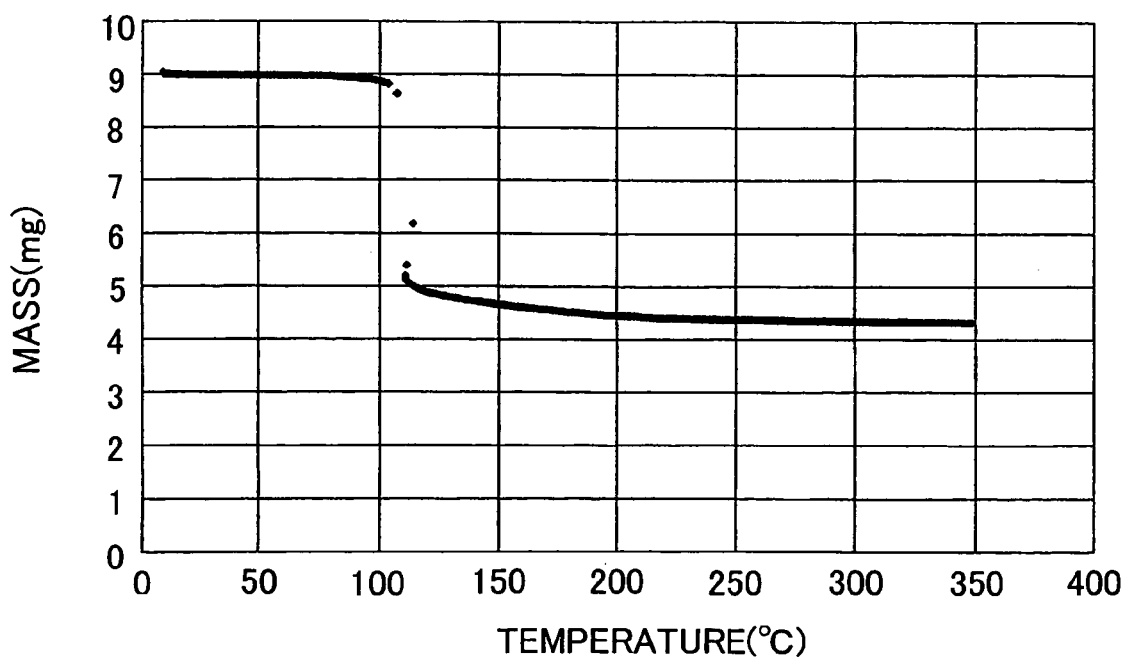
FIG. 12 is a graph that shows the measurement results of the thermogravimetric analysis of silver methyl acetoacetate in a yet further example of the invention.

Diethanolamine (4.4 g) was dissolved in water (5 mL), and this solution was added to the ether solution of α-ethylacetoacetic acid while cooling with ice. Next, a solution of silver nitrate (6.8 g) dissolved in water (8 mL) was added dropwise. The white precipitate that precipitated was filtered off, washed with ice water and then isopropanol, and dried, yielding silver α-methylacetoacetate as a white precipitate (yield 6.7 g). FIG. 6 shows the infrared absorption spectrum (IR) of the silver α-methylacetoacetate that was obtained. IR:1700 cm$^{-1}$, 1547 cm$^{-1}$.

The NMR (in deuterated DMSO) of the silver α-ethylacetoacetate that was obtained is shown below.

| | |
|---|---|
| 0.83 ppm 3H t | |
| 1.67 ppm 2H quintet | |
| 2.15 ppm 3H s | |
| 3.25 ppm 1H t | J = 7 Hz |

Working Example 7

Thermogravimetric Analysis

Thermogravimetric analysis (TGA) of the silver β-ketocarboxylate samples synthesized in working examples 1 through 6 was performed using a thermal analysis device (trade name GTA50: made by Shimadzu Corporation). In each case, the measurement condition was 10° C./min rate of a rise in temperature and at atmospheric pressure. The amount of sample was silver isobutyrylacetate 8.63 mg, silver acetoacetate 6.77 mg, silver propionylacetate 5.24 mg, silver benzoylacetate 5.35 mg, silver α-methylacetoacetate 6.18 mg, and silver α-ethylacetoacetate 9.05 mg. The results of the TGA measurement of the silver β-carboxylates of working examples 1 through 6 are shown in the graphs of FIGS. 7 through 12, respectively. Table 3 below shows the change in sample mass due to heating, which is obtained from the TGA results. In Table 3, the silver content of the synthesized silver β-ketocarboxylates (theoretical values) and the residual mass after thermal decomposition of the samples (experimental values) were calculated by the following equations.

silver content (%)=(atomic weight of silver/molecular weight of silver β-ketocarboxylate)×100 residual mass (%)=(A/B)×100

A: mass of sample after thermal decomposition (mg)
B: mass of sample used in TGA measurement (mg)

TABLE 3

| | silver β-ketocarboxylate | decomposition temperature (° C.) | silver content (%) | residual mass (%) |
|---|---|---|---|---|
| Working Example 1 | silver isobutyrylacetate | 145 | 45.6 | 51.9 |
| Working Example 2 | silver acetoacetate | 110 | 51.6 | 53.0 |
| Working Example 3 | silver propionylacetate | 130 | 48.4 | 55.6 |
| Working Example 4 | silver benzoylacetate | 120 | 39.9 | 70.9 |
| Working Example 5 | silver α-methylacetoacetate | 95 | 48.4 | 55.8 |
| Working Example 6 | silver α-ethylacetoacetate | 110 | 45.6 | 58.0 |

It can be understood from the results of FIGS. 7 through 12 that with the silver β-ketocarboxylates of the working examples, decomposition occurred abruptly at a heating temperature less than 210° C. and it was possible to form the metal silver rapidly, and also that it is possible to adjust the decomposition temperature by changing the silver β-ketocarbonyl group. Further, because the residual masses after thermal decomposition of the silver β-ketocarboxylates were values near the theoretical value of the silver content, it was understood that the silver β-ketocarboxylates sufficiently decomposed at their decomposition temperature and that metal silver was formed.

Working Example 8

Metal silver films were formed using the silver β-ketocarboxylates synthesized in working examples 1 and 3 through 6, and their conductivity was assessed.

Measuring Resistance

First, the silver β-ketocarboxylates that were synthesized in working examples 1, 3 and 4 were dispersed in the media shown in Table 4 below to prepare dispersions, each with a silver β-ketocarboxylate concentration of 1 mol/L. Then, using a dropper or a spatula, the dispersions were applied onto a slide glass with an applied area of (length 20 mm×width 3.5 mm) and an applied amount of 0.02 mL. The silver α-methylacetoacetate that was synthesized in working example 5 was dissolved in 1-methyl-2-pyrrolidone to prepare a solution with a silver α-methylacetoacetate concentration of 1.5 mol/L. Then, using a dropper, the solution was applied to a slide glass with an applied area of (length 50 mm×width 3.5 mm) and an applied amount of 0.04 mL. The silver α-ethylacetoacetate that was synthesized in working example 6 was dissolved in DMSO to prepare a solution with a silver α-ethylacetoacetate concentration of 1.5 mol/L. Then, using a dropper, the solution was applied to a slide glass with an applied area of (length 50 mm×width 3.5 mm) and an applied amount of 0.04 mL.

The slide glasses to which the dispersion liquid or solution was applied were heated at 80° C. for 30 minutes, and then the resistance of the applied film was measured with a multimeter (trade name R6871E-DC Digital Multimeter: made by Advantest Corporation). In all cases, the result was non-conductive.

TABLE 4

| | silver β-ketocarboxylate | solvent |
|---|---|---|
| Working Example 1 | silver isobutyrylacetate | butoxyethanol |
| Working Example 3 | silver propionylacetate | acetoxymethoxypropane |
| Working Example 4 | silver benzoylacetate | butoxyethanol |
| Working Example 5 | silver α-methylacetoacetate | 1-methyl-2-pyrrolidone |
| Working Example 6 | silver α-ethylacetoacetate | DMSO |

Next, the slide glasses to which the dispersion liquid or solution was applied were placed in an oven pre-heated to the temperatures listed below and left undisturbed for 30 minutes. The slide glasses were removed and cooled to room temperature, and then the resistance of the metal silver film that was formed was measured with the multimeter. The result of these measurements is shown in Table 5 below.

TABLE 5

| | silver β-ketocarboxylate | holding temperature (° C.) | resistance (Ωcm) |
|---|---|---|---|
| Working Example 1 | silver isobutyrylacetate | 170 | $2.7 \times 10^{-4}$ |
| | | 200 | $8.3 \times 10^{-5}$ |
| Working Example 3 | silver propionylacetate | 170 | $7.8 \times 10^{-3}$ |
| Working Example 4 | silver benzoylacetate | 210 | $4.6 \times 10^{-4}$ |
| Working Example 5 | silver α-methylacetoacetate | 160 | $9.0 \times 10^{-5}$ |
| Working Example 6 | silver α-ethylacetoacetate | 160 | $1.9 \times 10^{-4}$ |

As shown by Table 5, the resistances of the metal silver films formed using the silver β-ketocarboxylates were on the order of approximately $10^{-5}$ to $10^{-3}$ Ωcm, and from this it was clear that the metal silver films are sufficiently capable of being used as conductive material.

INDUSTRIAL APPLICABILITY

Use of the metal silver forming material of the invention makes it possible to form metal silver at a low temperature that is less than approximately 210° C. Consequently, the forming material and the production method of the invention allow metal silver to be formed more readily than with conventional methods. Further, because processing can be conducted at a low temperature, it is for example possible to carry out the processing in combination with a resin that has low heat resistance, for example, and this broadens the applicability of the metal silver and makes it extremely useful.

The invention claimed is:

1. A silver β-ketocarboxylate represented by Formula (1) below:

[Chemical Formula 1]

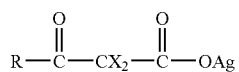

(1)

wherein in Formula (1), R is a straight, branched or cyclic saturated or unsaturated $C_1$ to $C_{20}$ aliphatic hydrocarbon group, $R^1$—$CY_2$—, $CY_3$—, $R^1$—CHY—, $R^2O$—, a phenyl group, a phenyl group with one or more substituent groups, $R^5R^4N$—, a hydroxyl group (—OH), an amino group (—NH$_2$), or $(R^3O)_2CY$—;

wherein the Y groups are identical or different, and each is a fluorine atom, a chlorine atom, a bromine atom, or a hydrogen atom, $R^1$ is a straight, branched or cyclic saturated or unsaturated $C_1$ to $C_{19}$ aliphatic hydrocarbon group, or a phenyl group, $R^2$ is a straight, branched or cyclic saturated or unsaturated $C_1$ to $C_{20}$ aliphatic hydrocarbon group, $R^3$ is a straight, branched or cyclic saturated or unsaturated $C_1$ to $C_{16}$ aliphatic hydrocarbon group, and $R^4$ and $R^5$ are identical or different, and each is a straight, branched or cyclic saturated or unsaturated $C_1$ to $C_{18}$ aliphatic hydrocarbon group;

wherein in Formula (1), the X groups are identical or different, and each is a hydrogen atom, a straight, branched or cyclic saturated or unsaturated $C_1$ to $C_{20}$ aliphatic hydrocarbon group, $R^6O$—, $R^6S$—, $R^6$—CO—, $R^6$—CO—O—, a halogen (fluorine, chlorine, bromine, iodine), a benzyl group, a phenyl group, a phenyl group or a benzyl group that has one or more substituent groups, a cyano group (—C≡N), a N-phthaloyl-3-aminopropyl group, or a 2-ethoxyvinyl group ($C_2H_5$—O—CH═CH—); and wherein $R^6$ is a straight, branched or cyclic saturated or unsaturated $C_1$ to $C_{10}$ aliphatic hydrocarbon group, a thiophene group ($C_4H_3S$—), a phenyl group, a diphenyl group, or a phenyl group or a diphenyl group that has one or more substituent groups.

2. The silver β-ketocarhoxylate according to claim 1, wherein the silver β-ketocarboxcylate is at least one selected from the group consisting of silver isobutyrylacetate, silver benzoylacetate, silver acetoacetate, silver propionylacetate, silver α-methylacetoacetate, and silver α-ethylacetoacetate.

3. A material for forming metal silver that includes silver β-ketocarboxylate.

4. A material for forming metal silver that includes silver β-ketocarboxylate, wherein the silver β-ketocarboxylate is the silver β-ketocarboxylate according to claim 1.

5. The material for forming metal silver according to claim 3, wherein the forming material is a dispersion or a solution in which the silver β-ketocarboxylate is dispersed or dissolved in a medium.

6. A method of producing metal silver, comprising: a step of heating a material for forming metal silver; wherein the forming material is the forming material including silver β-ketocarboxylate according to claim 3.

7. The method of producing metal silver according to claim 6, wherein the heating temperature is in a range of 60 to 210° C.

8. The method of producing metal silver according to claim 6, wherein the silver β-ketocarboxylate is silver isobutyrylacetate, and the heating temperature is in a range of 145 to 165° C.

9. The method of producing metal silver according to claim 6, wherein the silver β-ketocarboxylate is silver benzoylacetate, and the heating temperature is in a range of 120 to 140° C.

10. The method of producing metal silver according to claim 6, wherein the silver β-ketocarboxylate is silver acetoacetate, and the heating temperature is in a range of 110 to 130° C.

11. The method of producing metal silver according to claim 6,
wherein the silver β-ketocarboxylate is silver propionylacetate, and the heating temperature is in a range of 130 to 150° C.

12. The method of producing metal silver according to claim 6,
wherein the silver β-ketocarboxylate is silver α-methylacetoacetate, and the heating temperature is in a range of 90 to 120° C.

13. The method of producing metal silver according to claim 6,
wherein the silver β-ketocarboxylate is silver α-ethylacetoacetate, and the heating temperature is in a range of 90 to 120° C.

14. The method of producing metal silver according to claim 6,
wherein the forming material is applied onto a base material and subjected to heating, forming a metal silver film.

15. The method of producing metal silver according to claim 14,
wherein the metal silver film is connection wiring on the base material.

16. The method of producing metal silver according to claim 14,
wherein the base material is a resin base material.

17. The production method according to claim 6,
wherein a mixture containing the forming material and a resin is provided, and this is subjected to heating so as to form metal silver in the resin and carry out resin molding.

18. A method of producing silver β-ketocarboxylate, comprising:
a step of reacting a β-ketocarboxylic acid and a silver compound in a reaction solution whose water content is not more than 55 wt %, to form a silver β-ketocarboxylate.

19. The production method according to claim 18,
wherein in the reaction solution, the β-ketocarboxylic acid concentration is 0.1 to 5 mol/L and the silver compound concentration is 0.1 mol/L or more.

20. The production method according to claim 18,
wherein the β-ketocarboxylic acid and the silver compound are reacted in the presence of an amine.

21. The production method according to claim 20,
wherein an amine concentration of an amine solution that is added to the reaction solution is 2 mol/L or more.

22. The production method according to claim 20,
wherein a concentration of the amine in the reaction solution is 0.1 to 5 mol/L.

23. The production method according to claim 18,
wherein the silver compound concentration of a silver compound solution that is added to the reaction solution is 1 mol/L or more.

* * * * *